United States Patent
Klussmann et al.

(10) Patent No.: US 9,102,667 B2
(45) Date of Patent: Aug. 11, 2015

(54) N-ARYLAMINOMETHYLENE BENZOTHIOPHENONES FOR TREATMENT OF CARDIOVASCULAR DISEASE

(75) Inventors: Enno Klussmann, Berlin (DE); Walter Rosenthal, Kleinmachnow (DE); Jelena Milic, Berlin (DE); Martin W. Bergmann, Hamburg (DE)

(73) Assignee: FORSCHUNGSVERBUND BERLIN E.V., Berlin (DE)

( * ) Notice: Subject to any disclaimer, the term of this patent is extended or adjusted under 35 U.S.C. 154(b) by 0 days.

(21) Appl. No.: 13/980,057

(22) PCT Filed: Jan. 18, 2012

(86) PCT No.: PCT/EP2012/050742
§ 371 (c)(1),
(2), (4) Date: Jul. 17, 2013

(87) PCT Pub. No.: WO2012/098172
PCT Pub. Date: Jul. 26, 2012

(65) Prior Publication Data
US 2013/0289057 A1    Oct. 31, 2013

(30) Foreign Application Priority Data
Jan. 18, 2011 (DE) .......................... 10 2011 000 207

(51) Int. Cl.
| | | |
|---|---|---|
| *C07D 417/12* | (2006.01) | |
| *C07D 403/12* | (2006.01) | |
| *C07D 413/12* | (2006.01) | |
| *A61K 31/135* | (2006.01) | |
| *A61K 31/343* | (2006.01) | |
| *A61K 31/381* | (2006.01) | |
| *A61K 31/428* | (2006.01) | |
| *A61K 31/4402* | (2006.01) | |
| *A61K 31/4406* | (2006.01) | |
| *A61K 31/4427* | (2006.01) | |
| *A61K 31/47* | (2006.01) | |
| *A61K 31/4709* | (2006.01) | |
| *C07D 333/64* | (2006.01) | |
| *C07D 409/12* | (2006.01) | |

(52) U.S. Cl.
CPC ............ *C07D 417/12* (2013.01); *A61K 31/135* (2013.01); *A61K 31/343* (2013.01); *A61K 31/381* (2013.01); *A61K 31/428* (2013.01); *A61K 31/4402* (2013.01); *A61K 31/4406* (2013.01); *A61K 31/4427* (2013.01); *A61K 31/47* (2013.01); *A61K 31/4709* (2013.01); *C07D 333/64* (2013.01); *C07D 403/12* (2013.01); *C07D 409/12* (2013.01); *C07D 413/12* (2013.01)

(58) Field of Classification Search
None
See application file for complete search history.

(56) References Cited

U.S. PATENT DOCUMENTS
2008/0031818 A1* 2/2008 Bush et al. .................... 424/9.2

FOREIGN PATENT DOCUMENTS
| WO | WO96/12718 | 5/1996 |
|---|---|---|
| WO | WO2010/042225 | 4/2010 |

OTHER PUBLICATIONS

Chemical Abstracts Registry No. 414906-37-9, indexed in the Registry file on STN May 13, 2002.*
Pub Chem CID 5407360, created Jul. 9, 2005.*
PubChem CID 5512456—National Center for Biotechnology Information. PubChem Compound Database; CID=5512456, http://pubchem.ncbi.nlm.nih.gov/summary/summary.cgi?cid=5512456 (accessed Mar. 30, 2015), create date Jul. 11, 2005.*
Database Registry [Online] Chemical Abstracts Service, Columbus, Ohio; Apr. 28, 2004, TimTec, Inc, Database accession No. 677294-52-9 RN 677294-52-9 abstract.
Asche C et al, "Synthesis, antitumour activity and structure-activity relationships of 5H-benzo[b]carbazoles", Bioorganic & Medicinal Chemisty, vol. 13, No. 3; Feb. 1, 2005, pp. 819-837.
J.A. Zahra et al, "An alternative synthesis of 2-(N-arylhydrazono)-1-benzothiophen-3-ones", Organic and Biomolecular Chemisty, vol. 1, 2003 (2003), pp. 822-825.

* cited by examiner

*Primary Examiner* — Laura L. Stockton
(74) *Attorney, Agent, or Firm* — JMB Davis Ben-David

(57) ABSTRACT

The invention relates to N-arylaminomethylenebenzothiophenones of General Formula (I) for use as a drug for the treatment of cardiovascular diseases:

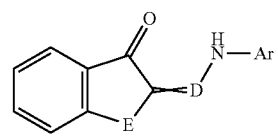

wherein E is S, O, or $CH_2$, D is CH or NH, and Ar is a phenyl or naphtyl moiety substituted by an electron-withdrawing group, an unsubstituted heteroaryl residue, or a heteroaryl residue substituted by alkyl or an electron-withdrawing group.

17 Claims, 6 Drawing Sheets

A

B

C

D

N-ARYLAMINOMETHYLENE BENZOTHIOPHENONES FOR TREATMENT OF CARDIOVASCULAR DISEASE

CROSS-REFERENCE TO RELATED APPLICATIONS

This is the U.S. National Stage of International Application No. PCT/EP2012/050742, filed Jan. 18, 2012, which was published in English under PCT Article 21 (2), which in turn claims the benefit of Germany Patent Application No. 10 2011 000 207.3, filed Jan. 18, 2011.

DESCRIPTION

The present invention relates to the area of N-arylaminomethylene benzothiophenones for treatment of cardiovascular disease.

Heart failure and high blood pressure (hypertension) are the most common causes of death worldwide. Heart failure in particular represents a widespread disease that is not treatable by pharmaceutical intervention in a satisfactory way. The development of new pharmaceuticals with better efficacy and significantly reduced side effects is needed.

A-kinase-anchoring proteins (AKAPs) form a group of structurally diverse proteins. They can bind to the regulatory subunit of protein kinase A (PKA), localize intracellularly and are involved in a variety of signal transduction pathways (Skroblin et al., *International Review of Cell and Molecular Biology* 283, 235-330 [2010]). In particular, the alpha and delta isoforms of AKAP18 have important roles in regulating the contraction of heart muscle cells and the water reabsorption in the main cells of the collecting duct of the kidneys.

WO2006122546 shows compounds that were found to disrupt the interaction between the protein AKAP18δ and the RII subunit of the PKA in an in-vitro screen. One of the compounds shown therein is a benzothiophenone compound, 4-[[(z)-(3-oxobenzothiophene-2-ylidene)methyl]amino]phenol.

The object of the present invention is to provide new compounds that are suitable as drugs for the treatment of cardiovascular diseases.

A structure-activity study of the previously mentioned benzothiophenone (VI) revealed surprisingly that compounds with the common feature of an aminomethylene-benzothiophenone—or an analogous scaffold—substituted at the amino nitrogen with an aromatic compound having at least one electron-withdrawing group, or with a heteroaromatic compound, inhibit the AKAP-PKA interaction. This correlation was initially found in several in-vitro systems that assayed the isolated protein components, and could be confirmed both in cell culture assays that study AKAP-PKA-dependent processes (redistribution of the AQP2 water channel) as well as in indication-relevant animal models.

The efficacy of the pharmaceutical compounds studied both in the TAC (transverse aortic restriction) model as well as in the SIADH (syndrome of inappropriate antidiuretic hormone secretion) model shows the availability of compounds according to the invention both for the treatment of (even severe) heart failure as well as for the treatment of SIADH (Schwartz-Bartter syndrome).

The compounds of the invention can be used for all indications that are associated with hyponatremia as a result of excessive water retention. This includes in particular heart failure, SIADH and cirrhosis of the liver, which can be triggered by different underlying diseases such as alcoholism, autoimmune diseases of the liver, or tumors. Water retention during pregnancy is a further indication.

Indicated in particular is the treatment of advanced-stage heart failure in Classes I through IV, preferably in Classes II, III, and in particular IV, following the functional classification system developed by the New York Heart Association (NYHA).

In the context of the present description, the term alkyl or alkyl group means saturated hydrocarbons comprising one to ten carbon atoms, which may be present in a branched, linear, or cyclic structure, or a cyclic structure with side chains. The term alkyl also encompasses partially unsaturated hydrocarbons, e.g., propenyl. Examples of alkyls are methyl, ethyl, isobutyl, pentyl, n-hexyl or cyclohexyl. The term alkyl also encompasses heteroalkyl groups.

In the context of the present description, the terms heteroalkyl or heteroalkyl group mean chains or cycles or combinations of chains and cycles of carbon, oxygen, nitrogen, and sulfur atoms that are bonded by single or double bonds. Examples of straight alkyl residues are morpholine residue, piperidinyl residue, or cyclic sugars such as ribose. $C_1$-$C_4$-alkyl means an alkyl group containing up to 4 carbon atoms, such as methyl, ethyl, 1- or 2-propyl, n-, tert- or isobutyl.

O-alkyl groups are alkyl ethers with the meaning of alkyl given above.

In the context of the present description, the term aryl means a cyclic aromatic unsaturated hydrocarbon. Heteroaryl compounds as used in the context of the present description are those aryls that feature nitrogen, oxygen, or sulfur atoms on the ring in addition to carbon atoms.

Examples of heteroaryl residues are pyrrole (azole), 1,2- and 1,3-diazole, the thiodiazoles (e.g., 1,2,5-, 1,2,3-), furan, thiophene, indole and its O— and S-homologues, indolizine, or pyridine.

Alkyl, heteroalkyl, aryl, and heteroaryl can also each be substituted by groups containing nitrogen, e.g., such as primary, secondary, or tertiary amines, imides, amides, isocyanides, isocyanates, or hydrazides; as well as groups containing oxygen such as alcohols, ethers, carbonyls, carboxylic acids and esters, or their sulfur homologues.

Halogens are fluorine, chlorine, bromine and iodine.

SUMMARY OF THE INVENTION

According to a first aspect of the invention, a compound according to General Formula I is provided for use as a drug for the treatment of cardiovascular diseases,

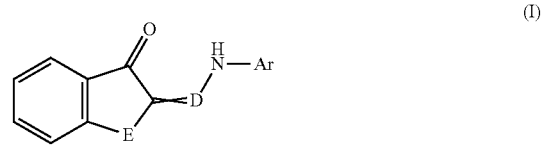

(I)

wherein:
E is S, O, or $CH_2$;
D is CH, or NH,
and Ar is
   a phenyl or naphtyl moiety substituted by an electron-withdrawing group,
   an unsubstituted heteroaryl residue, or a heteroaryl residue substituted by alkyl or an electron-withdrawing group.

According to a second aspect of the invention, a compound of General Formula V

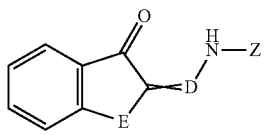

(V)

is provided as a drug, where
E is S (sulfur), O (oxygen), or CH$_2$ (methylene),
D is CH or NH, and
Z is a pentayclic heteroaryl moiety selected from imidazole, oxazole, thiazole, thiadiazole, benzimidazole, benzoxazole, benzothiazole, and wherein the pentacyclic heteroaryl moiety is optionally substituted by one or more substituents selected from the group comprising a halogen, a carboxylic acid or its C1-, C2-, C3- or C4 alkyl ester, a carboxylic acid amide, carboxamidine, a nitrile, isonitrile, cyanate, isocyanate, thiocyanate, isothiocyanate, a nitro group or a mono-, di- or trifluoromethane group or a C1-, C2-, C3- or C4 alkoxide moiety.

According to a third aspect of the invention, the compounds of the second aspect of the invention are provided as such.

DETAILED DESCRIPTION OF THE INVENTION

According to the first aspect of the invention, a compound according to General Formula I is provided for use as a drug for the treatment of cardiovascular diseases, one particular indication considered herein being heart failure in New York Heart Association (NYHA) Classes I-IV, Classes II-IV, or Classes III and IV. The treatment of SIADH or excessive water retention are similarly considered to fall within the scope of the medical indication for which the compounds of the present invention are useful.

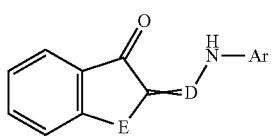

(I)

wherein:
E is S, O, or CH$_2$;
D is CH, or NH,
and Ar is
  a phenyl or naphtyl moiety substituted by an electron-withdrawing group,
  an unsubstituted heteroaryl residue, or a heteroaryl residue substituted by alkyl or an electron-withdrawing group.

While studying the structure-activity profile of a compound (VI, see below) comprising a 4-OH-phenyl as Ar group, it was found that the nitrogen substituent must be an aromatic ring, that in the cases where Ar is phenyl, an electron-withdrawing group adds to the activity while electron-donating groups such as OH or O-alkyl abrogate activity, and that generally, five-membered aromatic heterocycles increase activity of the compound. Thiazole rings as Ar may even be substituted by O-alkyl rings without losing all of their activity, however the most active species were found to contain electron-withdrawing groups. The two most active representatives were cyano- and nitro-substituted thiazoles.

According to one embodiment, the electron-withdrawing group is selected from halogen, a carboxylic acid or its C1-C4 alkyl ester, a carboxylic acid amide, a carboxamidine, a nitrile, isonitrile, cyanate, isocyanate, thiocyanate or isothiocyanate, a nitro group or a mono-, di- or trifluoromethane group.

In one embodiment, Ar is an aromatic pentacyclic structure with at least nitrogen as a ring member, in particular an aromatic pentacyclic structure with one nitrogen atom and at least one further heteroatom from the group of nitrogen, oxygen, or sulfur as a member.

In one embodiment, the heteroaryl residue is one of the moieties of Table 1 column A.

In one embodiment, the heteroaryl residue is one of the moieties of Table 1 column B.

The compounds shown in Table 2 are especially preferred embodiments of this first aspect of the invention.

TABLE 1

| No. | A | B |
|---|---|---|
| 1 | -2-, -4-, or -5-imidazoles, if needed substituted with C$_1$-C$_4$-alkyl; | -2-imidazole |
| 2 | -2-, -4-, -5-, -6-, or -7-benzimidazoles, optionally C-substituted with C$_1$-C$_4$-alkyl; | -2-benzimidazole |
| 3 | N-alkylated -2-, -4-, -5-, -6-, or -7-benzimidazoles; | -2-(1-methyl)benzimidazole |
| 4 | -2-, -4-, or -5-alkyloxazoles | -2-(4-methyl)-oxazole |
| 5 | pure or mixed -2-, -4-, -5-, -6-, or -7-halogenbenzoxazoles | -2-(5-chloro)-1,3-benzoxazole |
| 6 | -2-, -4-, or -5-thiazoles | -2-thiazole |
| 7 | 2-, 3- or 4-alkylated -2-, -4-, or -5-thiazoles | -2-(4-methyl)thiazole |

TABLE 1-continued

| No. | A | B |
|---|---|---|
| | | -2-(5-methyl)thiazole |
| 8 | -2-, -4-, or -5-thiazolecarbonitriles | -2-thiazole-5-carbonitrile |
| 9 | Thialzole carboxamidines | -2-thiazol-5-carboxamidine |
| 10 | Thiazole carboxylic acid amides | -2-thiazole-5-carboxylic acid amide |
| | | N-methyl-2-thiazole-5-carboxylic acid amide |
| 11 | -2-thiazole-carboxylic acids and -2-thiazole-carboxylic acid esters | -2-thiazole-5-carboxylic acid |
| | | -2-thiazole-4-carboxylic acid methylester |
| | | -2-thiazole-5-carboxylic acid methylester |
| 12 | phenylthiazoles | -2-(4-methyl)thiazole |
| 13 | -2-, -4-, -5-, -6-, or -7-benzothiazoles or halogenbenzothiazoles | -2-1,3-benzothiazole |
| | | -5-1,3-benzothiazole |
| 14 | pure or mixed -2-, -4-, -5-, -6-, or -7-halogenalkylbenzothiazoles | -2-(6-trifluoromethyl)-1,3-benzothiazole |
| 15 | pure or mixed -2-, -4-, -5-, -6-, or -7-alkyloxybenzothiazoles | -2-(6-methoxy)-1,3-benzothiazole |
| 16 | -2-, -4-, -5-, -6-, or -7-nitrobenzothiazoles | -2-(6-nitro)-1,3-benzothiazole |
| 17 | pure or mixed -2-, -4-, -5-, -6-, or -7-halogenbenzoxazoles | -2-(4,6-fluoro)-1,3-benzothiazole |
| | | -2-(6-bromo)-1,3-benzothiazole |
| 18 | -3 or -5-(1,2,4)thiodiazoles or, -4 or 5-(1,2,3)thiodazoles; -2- or -5-(1,3,4)thiodiazoles | -5-(1,2,4-thiodiazole) |

TABLE 1-continued

| No. | A | B |
|---|---|---|
|  |  | 2-(1,3,4-thiodiazole) 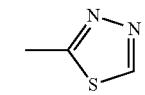 |
| 19 | -2- or -5-halogenthiadiazoles | -2-(5-bromo-1,3,4-thiodiazole) 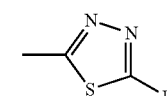 |
| 20 | -2-, -3-, or -4-nitrophenols | -2-(4-nitrophenol) 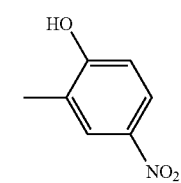 |
| 25 | -2-, -3-, or -4-benzoic acid | 4-benzoic acid 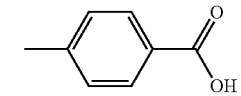 |
| 26 | -2-, -3-, or -4-benzoic acid alkylester | 4-benzoic acid methylester 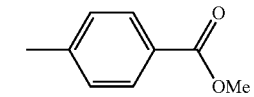 |
| 27 | halogenalkyl-halogenphenyls | -2-(1-chloro)-4-trifluoromethylbenzene 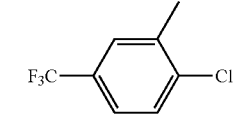 |
| 31 | -2-, -3-, -4-, -5-, -6-, -7- or -8-quinoline | -8-quinoline 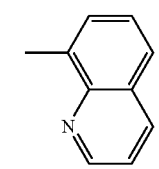 |
| 32 | pure or mixed -2-, -3-, -4-, -5-, -6-, -7-, or -8-halogenquinolines | -8-(5-chloro)-quinoline 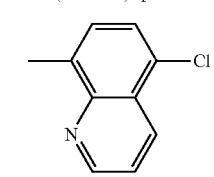 |
| 33 | -2-, -3-, -4-, -5-, or -6-halogenpyridines | -6(3-bromo)-pyridine 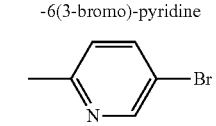 |
| 34 | -2-, -4-, or -5-pyrimidines | -2-pyrimidine 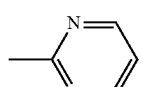 |
| 35 | -2-, -4-, -5-, -6-, -7- or -8-quinoline | -2-quinazoline 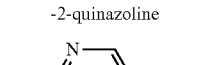 |

According to one embodiment, E is sulfur and Ar is a mono- or bicyclic heteroaryl residue.

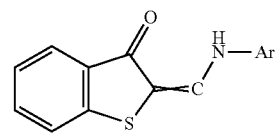

(II)

The representation of the double bond between the pentacyclic structure of the benzothiophene and D in Formulas I and II by an intersecting line signifies that both the E and the Z conformations of the double bond are within the scope of the formula. Where D=CH, for example, both the forms I-E and I-Z are likely to be in equilibrium where possible:

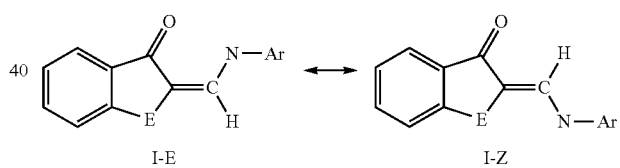

For certain embodiments of the invention for which D=CH, equilibrium of the E and Z conformation is presumably reached in aqueous solution by means of an enolate imine intermediate stage, in which the bond between the pentacyclic structure and methylene carbon is freely rotatable (R1 to R4 are not drawn in for clarity):

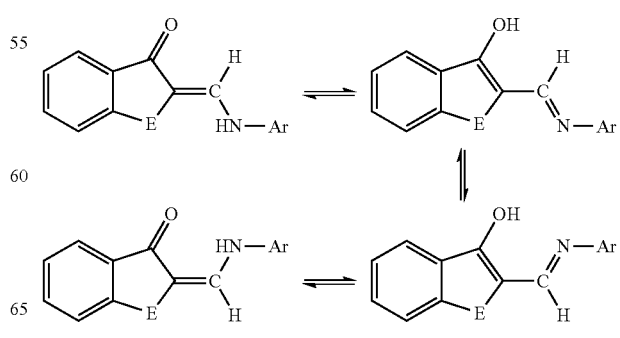

In water, the equilibrium is on the side of the Z-conformers. Preferred embodiments of all aspects of the invention are compounds for which D=CH and the double bond is present in Z-conformation (see I-Z).

According to one embodiment of the first aspect of the invention, a compound provided for treatment of heart disease is selected from Table 2, or is any of III and IV:

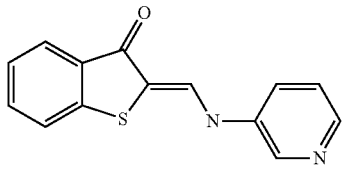

(III)

2-[(3-pyridylamino)methylene]benzothiophene-3-one (2E or 2Z) (III);

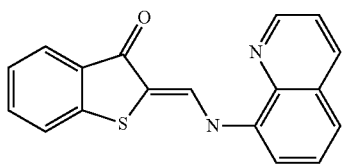

(IV)

(2Z)-2-[(8-quinolylamino)methylene]benzothiophene-3-one (IV).

According to a second aspect of the invention, a compound of General Formula V

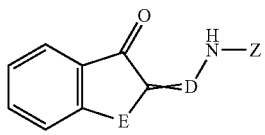

V is provided as a drug, where
E is S (sulfur), O (oxygen), or $CH_2$ (methylene),
D is CH or NH, and
Z is a pentayclic heteroaryl moiety selected from imidazole, oxazole, thiazole, thiadiazole, benzimidazole, benzoxazole, benzothiazole, and wherein the pentacyclic heteroaryl moiety is optionally substituted by one or more substituents selected from the group comprising a halogen, a carboxylic acid or its C1-, C2-, C3- or C4 alkyl ester, a carboxylic acid amide, carboxamidine, a nitrile, isonitrile, cyanate, isocyanate, thiocyanate, isothiocyanate, a nitro group or a mono-, di- or trifluoromethane group or a C1-, C2-, C3- or C4 alkoxide moiety.

In one embodiment of this aspect of the invention, E is sulfur.

In one embodiment of this aspect of the invention, D is CH.

In one embodiment of this aspect of the invention, D is N.

In one embodiment, Z is a moiety selected of numbers 1, 2, 3, 4, 5, 6, 7, 8, 9, 10, 13, 14, 15, 16, 17, 18, or 19 of Table 1, Column A.

In one embodiment, Z is a moiety selected of numbers 1, 2, 3, 4, 5, 6, 7, 8, 9, 10, 13, 14, 15, 16, 17, 18, or 19 of Table 1, Column B.

The compounds 1 to 32 and 50 to 55 and 57 of Table 2 are especially preferred embodiments of this second aspect of the invention.

According to a third aspect of the invention, a compound of General Formula V

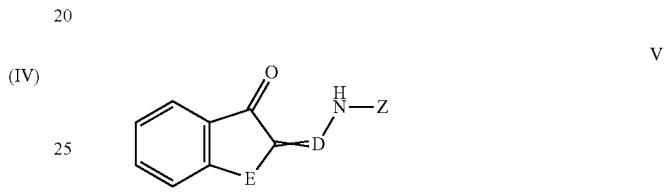

V is provided, where
E is S (sulfur), O (oxygen), or $CH_2$ (methylene),
D is CH or NH, and
Z is a pentayclic heteroaryl moiety selected from imidazole, oxazole, thiazole, thiadiazole, benzimidazole, benzoxazole, benzothiazole, and wherein the pentacyclic heteroaryl moiety is optionally substituted by one or more substituents selected from the group comprising a halogen, a carboxylic acid or its C1-, C2-, C3- or C4-alkyl ester, a carboxylic acid amide, carboxamidine, a nitrile, isonitrile, cyanate, isocyanate, thiocyanate, isothiocyanate, a nitro group or a mono-, di- or trifluoromethane group or a C1-, C2-, C3- or C4 alkoxide moiety.

In one embodiment of this aspect of the invention, E is sulfur.

In one embodiment of this aspect of the invention, D is CH.

In one embodiment of this aspect of the invention, D is N.

In one embodiment, Z is a moiety selected of numbers 1, 2, 3, 4, 5, 6, 7, 8, 9, 10, 13, 14, 15, 16, 17, 18, or 19 of Table 1, Column A.

In one embodiment, Z is a moiety selected of numbers 1, 2, 3, 4, 5, 6, 7, 8, 9, 10, 13, 14, 15, 16, 17, 18, or 19 of Table 1, Column B.

The compounds 1 to 32 and 50 to 55 and 57 of Table 2 are especially preferred embodiments of this third aspect of the invention.

TABLE 2

| No. | Structure | IUPAC Name |
|---|---|---|
| 1 | 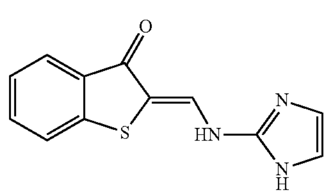 [SMILES: O=C1/C(=C/Nc2ncc[nH]2)Sc2ccccc21] | (2Z)-2-[(1H-imidazole-2-ylamino)methylene]benzothiophene-3-one<br>Activity: A |

TABLE 2-continued

| No. | Structure | IUPAC Name |
|---|---|---|
| 2 | 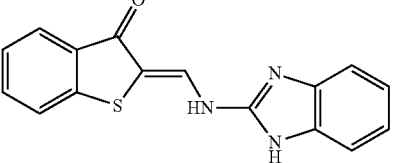 | (2Z)-2-[(1H-benzimidazole-2-ylamino)methylene]benzothiophene-3-one<br>Activity: A |
| 3 | 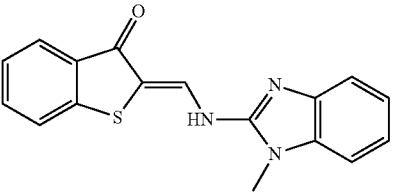 [SMILES: Cn1c(N/C=C2\Sc3ccccc3C2=O)nc2ccccc21] | (2Z)-2-[[(1-methylbenzimidazole-2-yl)amino]methylene]benzothiophene-3-one<br>Activity: A |
| 4 | 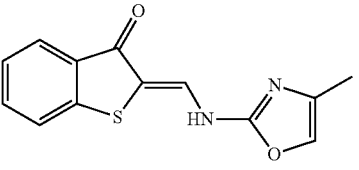 [SMILES: Cc1coc(N/C=C2\Sc3ccccc3C2=O)n1] | (2Z)-2-[[(4-methyloxazole-2-yl)amino]methylene]benzothiophene-3-one<br>Activity: AA |
| 5 | 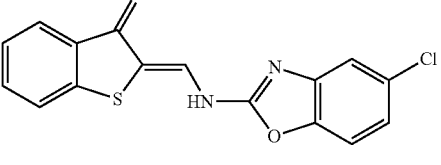 | (2Z)-2-[[(5-chloro-1,3-benzoxazole-2-yl)amino]methylene]benzothiophene-3-one<br>Activity: C |
| 6 | 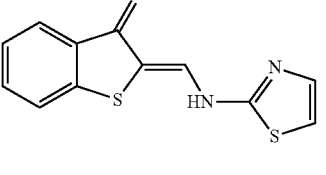 | (2Z)-2-[(thiazole-2-ylamino)methylene]benzothiophene-3-one<br>Activity: A |
| 10 | 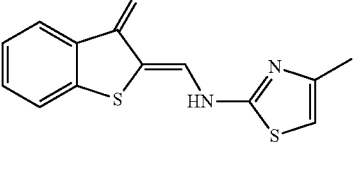 | (2Z)-2-[[(4-methylthiazole-2-yl)amino]methylene]benzothiophene-3-one |
| 11 | 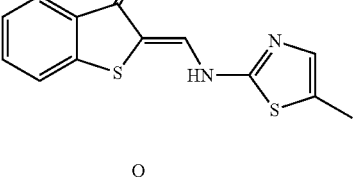 | (2Z)-2-[[(5-methylthiazole-2-yl)amino]methylene]benzothiophene-3-one<br>Activity: A |
| 12 | 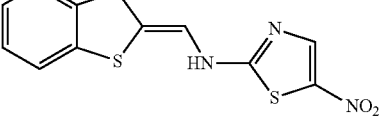 | (2Z)-2-[[(5-nitrothiazole-2-yl)amino]methylene]benzothiophene-3-one<br>Activity: AA+ |

TABLE 2-continued

| No. | Structure | IUPAC Name |
|---|---|---|
| 13 | 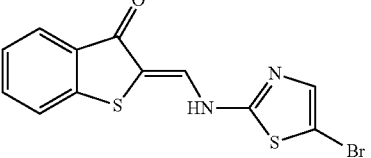 | (2Z)-2-[[(5-bromothiazole-2-yl)amino]methylene]benzothiophene-3-one<br>Activity: AA |
| 14 | 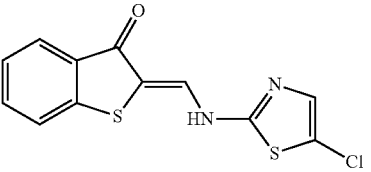 [SMILES: O=C1/C(=C/Nc2ncc(Cl)s2)Sc2ccccc21] | (2Z)-2-[[(5-chlorothiazole-2-yl)amino]methylene]benzothiophene-3-one<br>Activity: A |
| 15 | 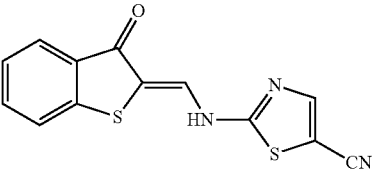 [SMILES: N#Cc1cnc(N/C=C2\Sc3ccccc3C2=O)s1] | 2-[[(z)-(3-oxobenzothiophene-2-ylidene)methyl]amino]thiazole-5-carbonitrile<br>Activity: AA+ |
| 16 | 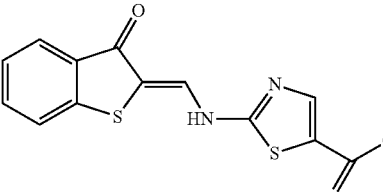 | 2-[[(z)-(3-oxobenzothiophene-2-ylidene)methyl]amino]thiazole-5-carboxylic acid<br>Activity: B |
| 17 | 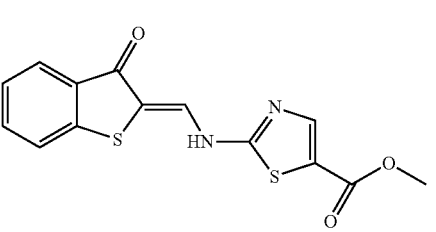 [SMILES: COC(=O)c1cnc(N/C=C2\Sc3ccccc3C2=O)s1] | 2-[[(z)-(3-oxobenzothiophene-2-ylidene)methyl]amino]thiazole-5-carboxylic acid methylester<br>Activity: A(A) |
| 18 | 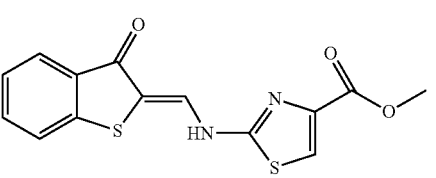 [SMILES: COC(=O)c1csc(N/C=C2\Sc3ccccc3C2=O)n1] | 2-[[(z)-(3-oxobenzothiophene-2-ylidene)methyl]amino]thiazole-4-carboxylic acid methylester<br>Activity: A |
| 19 | 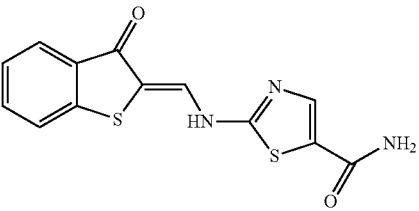 [SMILES: NC(=O)c1cnc(N/C=C2\Sc3ccccc3C2=O)s1] | 2-[[(z)-(3-oxobenzothiophene-2-ylidene)methyl]amino]thiazole-5- carboxylic acid amide<br>Activity: A |

TABLE 2-continued

| No. | Structure | IUPAC Name |
|---|---|---|
| 20 | 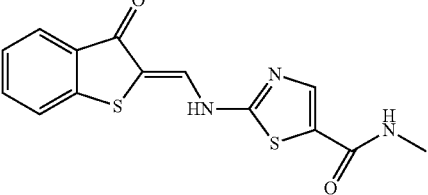 | n-methyl-2-[[(z)-(3-oxobenzothiophene-2-ylidene)methyl]amino]thiazole-5- carboxylic acid amide<br>Activity: B |
| 21 | 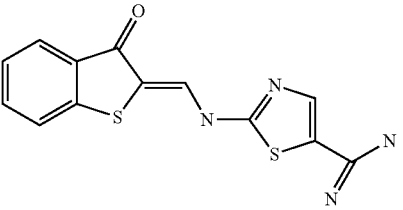 [SMILES: N=C(N)c1cnc(N/C=C2\Sc3ccccc3C2=O)s1] | 2-[[(Z)-(3-oxobenzothiophen-2-ylidene)methyl]amino]thiazole-5-carboxamidine<br>Activity: A/B |
| 23 | 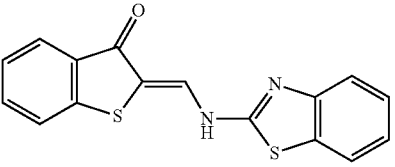 [SMILES: O=C1/C(=C/Nc2nc3ccccc3s2)Sc2ccccc21] | (2Z)-2-[(1,3-benzothiazol-2-ylamino)methylene]-benzothiophen-3-one<br>Activity A/B |
| 24 | 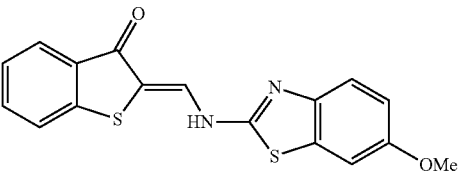 [SMILES: COc1ccc2nc(N/C=C3\Sc4ccccc4C3=O)sc2c1] | (2Z)-2-[[(6-methoxy-1,3-benzothiazole-2-yl)amino]methylene]benzothiophene-3-one<br>Activity: A |
| 25 | 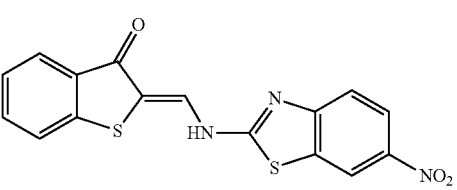 [SMILES: O=C1/C(=C/Nc2nc3ccc([N+](=O)[O-])cc3s2)Sc2ccccc21] | (2Z)-2-[[(6-nitro-1,3-benzothiazole-2-yl)amino]methylene]benzothiophene-3-one<br>Activity: B |
| 26 | 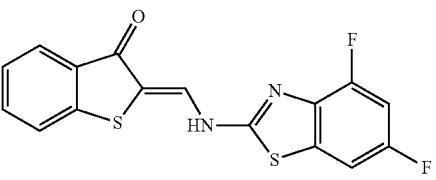 [SMILES: O=C1/C(=C/Nc2nc3c(F)cc(F)cc3s2)Sc2ccccc21] | (2Z)-2-[[(4,6-difluoro-1,3-benzothiazole-2-yl)amino]methylene]benzothiophene-3-one<br>Activity: C |
| 27 | 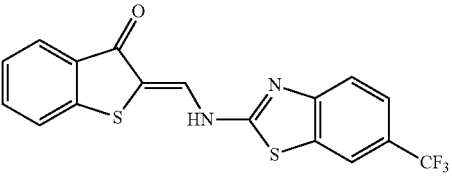 [SMILES: O=C1/C(=C/Nc2nc3ccc(C(F)(F)F)cc3s2)Sc2ccccc21] | (2Z)-2-[[[6-(trifluoromethyl)-1,3-benzothiazole-2-yl]amino]methylene]benzothiophene-3-one<br>Activity: C |
| 28 | 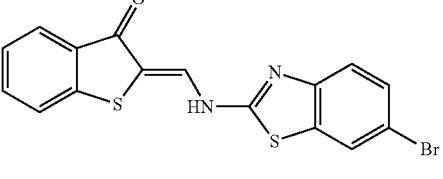 | (2Z)-2-[[(6-bromo-1,3-benzothiazole-2-yl)amino]methylene]benzothiophene-3-one<br>Activity: A |

TABLE 2-continued

| No. | Structure | IUPAC Name |
|---|---|---|
| 29 | 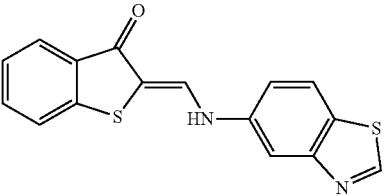 [SMILES: O=C1/C(=C/Nc2ccc3scnc3c2)Sc2ccccc21] | (2Z)-2-[(1,3-benzothiazole-5-ylamino)methylene]benzothiophene-3-one<br>Activity: C |
| 30 | 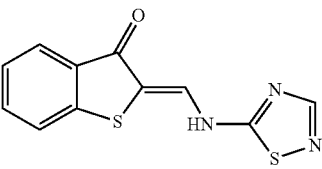 [SMILES: O=C1/C(=C/Nc2ncns2)Sc2ccccc21] | (2Z)-2-[(1,2,4-thiadiazol-5-ylamino)methylene]benzothiophene-3-one<br>Activity: A |
| 31 | 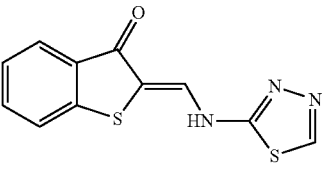 [SMILES: O=C1/C(=C/Nc2nncs2)Sc2ccccc21] | (2Z)-2-[(1,3,4-thiadiazol-2-ylamino)methylene]benzothiophene-3-one<br>Activity: A |
| 32 | 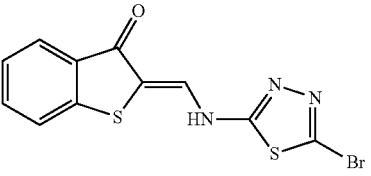 [SMILES: O=C1/C(=C/Nc2nnc(Br)s2)Sc2ccccc21] | (2Z)-2-[[(5-bromo-1,3,4-thiadiazol-2-yl)amino]methylene]benzothiophene-3-one<br>Activity: A |
| 33 | 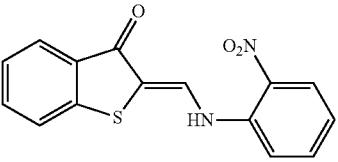 [SMILES: O=C1/C(=C/Nc2ccccc2[N+](=O)[O-])Sc2ccccc21] | (2Z)-2-[(2-nitroanilino)methylene]benzothiophene-3-one<br>Activity: A |
| 34 | 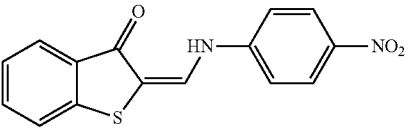 [SMILES: O=C1/C(=C\Nc2ccc([N+](=O)[O-])cc2)Sc2ccccc21] | (2e)-2-[(4-nitroanilino)methylene]benzothiophene-3-one<br>Activity: C |
| 35 | 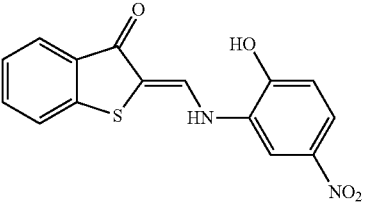 [SMILES: O=C1/C(=C/Nc2cc([N+](=O)[O-])ccc2O)Sc2ccccc21] | (2Z)-2-[(2-hydroxy-5-nitro-anilino)methylene]benzothiophene-3-one<br>Activity: C |
| 37 | 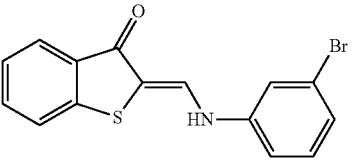 [SMILES: O=C1/C(=C/Nc2cccc(Br)c2)Sc2ccccc21] | (2Z)-2-[(3-bromoanilino)methylene]benzothiophene-3-one<br>Activity: C |

TABLE 2-continued

| No. | Structure | IUPAC Name |
|---|---|---|
| 39 | 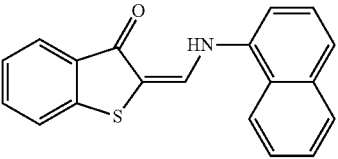 [SMILES: O=C1/C(=C\Nc2cccc3ccccc23)Sc2ccccc21] | (2e)-2-[(1-naphthylamino)methylene]benzothiophene-3-one<br>Activity: C |
| 42 | 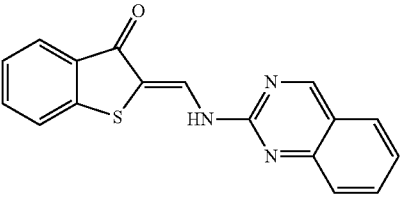 [SMILES: O=C1/C(=C/Nc2ncc3ccccc3n2)Sc2ccccc21] | (2Z)-2-[(chinazolin-2-ylamino)methylene]benzothiophene-3-one<br>Activity: C |
| 49 | 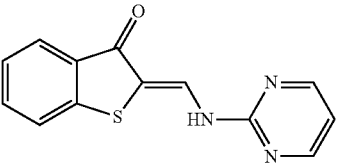 [SMILES: O=C1/C(=C/Nc2ncccn2)Sc2ccccc21] | (2Z)-2-[(pyrimidine-2-ylamino)methylene]benzothiophene-3-one<br>Activity: B |
| 50 | 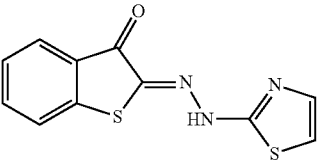 [SMILES: O=C1/C(=N/Nc2nccs2)Sc2ccccc21] | (2Z)-2-(thiazole-2-ylhydrazono)benzothiophene-3-one<br>Activity: AA+ |
| 51 | 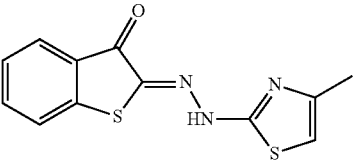 [SMILES: Cc1csc(N/N=C2\Sc3ccccc3C2=O)n1] | (2Z)-2-[(4-methylthiazole-2-yl)hydrazono]benzothiophene-3-one<br>Activity: AA+ |
| 52 | 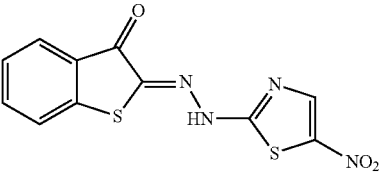 [SMILES: O=C1/C(=N/Nc2ncc([N+](=O)[O-])s2)Sc2ccccc21] | (2Z)-2-[(5-nitrothiazole-2-yl)hydrazono]benzothiophene-3-one<br>Activity: AA+ |
| 53 | 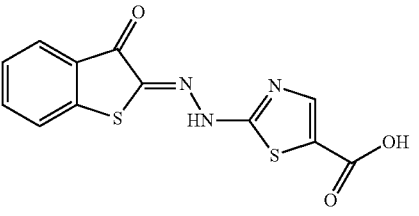 [SMILES: O=C(O)c1cnc(N/N=C2\Sc3ccccc3C2=O)s1] | 2-[(2Z)-2-(3-oxobenzothiophene-2-ylidene)hydrazino]thiazole-5-carboxylic acid<br>Activity: AA+ |
| 54 | 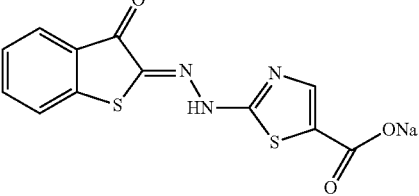 | sodium [2-[(2Z)-2-(3-oxobenzothiophene-2-ylidene)hydrazino]thiazole-5-carbonylate]<br>Activity: AA+ |

TABLE 2-continued

| No. | Structure | IUPAC Name |
|---|---|---|
| 55 | 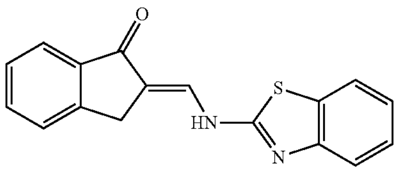 [SMILES: O=C1/C(=C/Nc2nc3ccccc3s2)Cc2ccccc21] | (2e)-2-[(1,3-benzothiazole-2-ylamino)methylene]indane-1-one<br>Activity: B |
| 56 | 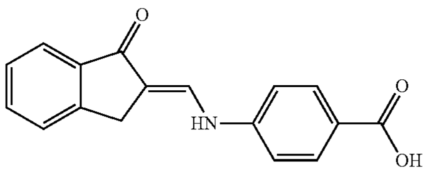 | 4-[[(e)-(1-oxoindan-2-ylidene)methyl]amino]benzoic acid<br>Activity: A |
| 57 | 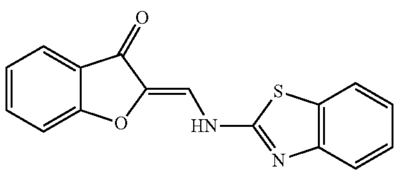 [SMILES: O=C1/C(=C/Nc2nc3ccccc3s2)Oc2ccccc21] | (2Z)-2-[(1,3-benzothiazole-2-ylamino)methylene]benzofuran-3-one<br>Activity: C |
| 58 | 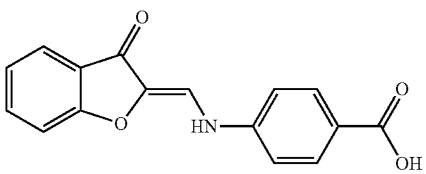 [SMILES: O=C(O)c1ccc(N/C=C2\Oc3ccccc3C2=O)cc1] | 4-[[(z)-(3-oxobenzofuran-2-ylidene)methyl]amino]benzoic acid<br>Activity: B/C |
| 59 | 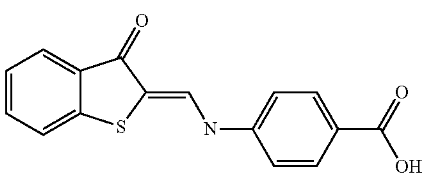 [SMILES: O=C(O)c1ccc(N/C=C2\Sc3ccccc3C2=O)cc1] | 4-[[(z)-(3-oxobenzothiophene-2-ylidene)methyl]amino]benzoic acid<br>Activity: B |

TABLE 3 compounds with no activity in AKAP-PKA disruption assays of Examples 1-3

| | | |
|---|---|---|
| 1 | | (2Z)-2-(anilinomethylene)benzothiophen-3-one |
| 2 | | (2Z)-2-[(2-hydroxyanilino)methylene]benzothiophen-3-one |
| 2a | | (2Z)-2-[(2-methoxyanilino)methylene]benzothiophen-3-one |

TABLE 3-continued compounds with no activity in AKAP-PKA disruption assays of Examples 1-3

| | | |
|---|---|---|
| 3 | | (2E)-2-[(4-ethoxyanilino)methylene]benzothiophen-3-one |
| 4 | | (2E)-2-[(2-methylanilino)methylene]benzothiophen-3-one |
| 5 | | (2Z)-5-ethoxy-2-(propylaminomethylene)benzothiophen-3-one |
| 6 | | (2Z)-2-(butylaminomethylene)-5-ethoxy-benzothiophen-3-one |
| 7 | | (2Z)-5-ethoxy-2-[(pentylamino)methylene]benzothiophen-3-one |
| 8 | | (2Z)-2-[(cyclohexylamino)methylene]-5-ethoxy-benzothiophen-3-one |
| 9 | | (2E)-5-ethoxy-2-[(isopropylamino)methylene]benzothiophen-3-one |
| 10 | | (2Z)-5-ethoxy-2-[[(4-fluorophenyl)methyl-amino]methylene]benzothiophen-3-one |
| 11 | | (2Z)-2-[[(4-chlorophenyl)methylamino]methylene]-5-ethoxy-benzothiophen-3-one |

TABLE 3-continued compounds with no activity in AKAP-PKA disruption assays of Examples 1-3

| 12 | 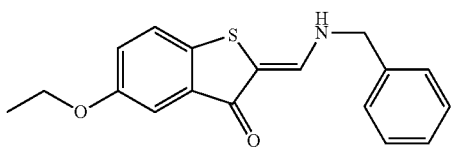 [SMILES: CCOc1ccc2c(c1)C(=O)/C(=C/NCc1ccccc1)S2] | (2Z)-2-[(benzylamino)methylene]-5-ethoxy-benzothiophen-3-one |

| 13 | 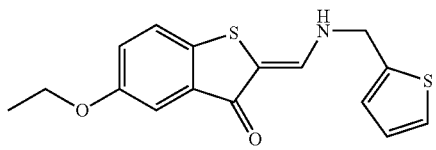 [SMILES: CCOc1ccc2c(c1)C(=O)/C(=C/NCc1cccs1)S2] | (2Z)-5-ethoxy-2-[(2-thienylmethyl-amino)methylene]benzothiophen-3-one |

| 14 | 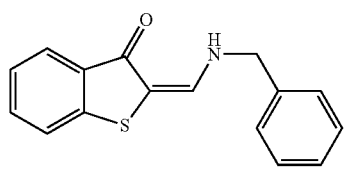 [SMILES: O=C1/C(=C\NCc2ccccc2)Sc2ccccc21] | (2E)-2-[(benzylamino)methylene]benzothiophen-3-one |

| 15 | 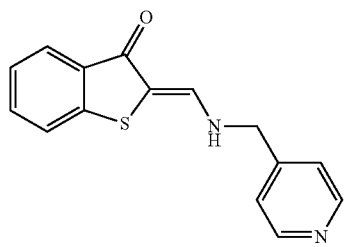 [SMILES: O=C1/C(=C/NCc2ccncc2)Sc2ccccc21] | (2Z)-2-[(4-pyridylmethyl-amino)methylene]benzothiophen-3-one |

| 16 | 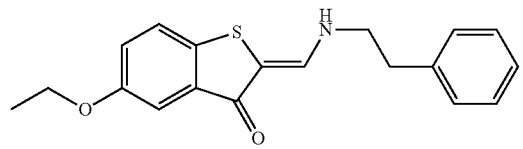 [SMILES: CCOc1ccc2c(c1)C(=O)/C(=C/NCCc1ccccc1)S2] | (2Z)-5-ethoxy-2-[(phenethyl-amino)methylene]benzothiophen-3-one |

| 17 | 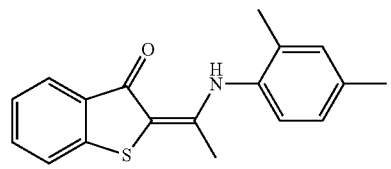 [SMILES: C/C(Nc1ccc(C)cc1C)=C1\Sc2ccccc2C1=O] | (2E)-2-[1-(2,4-dimethylanilino)ethylidene]benzo-thiophen-3-one |

| 18 | 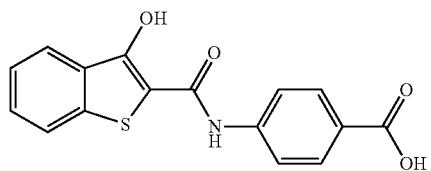 [SMILES: O=C(O)c1ccc(NC(=O)c2sc3ccccc3c2O)cc1] | 4-[(3-hydroxybenzothiophene-2-carbonyl)amino]benzoic acid |

| 19 | 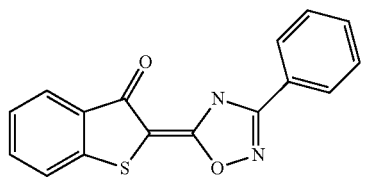 [SMILES: O=C1/C(=C2\NC(c3ccccc3)=NO2)Sc2ccccc21] | (2Z)-2-(3-phenyl-4H-1,2,4-oxadiazol-5-ylidene)benzothiophen-3-one |

The formulation of the compounds according to the invention into pharmaceutical preparations is performed in a manner known in the art, by converting the active ingredient or ingredients into the desired dosing form with the adjuvants usual in pharmaceutical formulation (*Remington's Pharmaceutical Science,* 15th ed. Mack Publishing Company, East Pennsylvania [1980]). The pharmaceutical formulations can exist in solid form, for example as tablets, coated tablets, pills, suppositories, capsules, transdermal systems, or in semisolid form, for example as ointments, creams, gels, suppositories, emulsions, or in liquid form, for example as solutions, tinctures, suspensions, or emulsions. In particular tablets, coated tablets, capsules, pills, powder, granules, pastilles, suspensions, emulsions, or solutions are a possibility for oral or peroral administration.

The dosage of the compound according to the invention as an active component of a administration form (application) depends on the age, weight, individual constitution, pharmacokinetic data, the administration form, and the precise indication. For a patient of ca. 70 kg, the daily dose must be measured at approximately 0.1 mg/kg to approximately 1000 mg, preferably from ca. 0.5 mg to ca. 100 mg/kg of the compound according to the invention.

According to another aspect of the compound, a procedure is provided to synthesize compounds of General Formula (X),

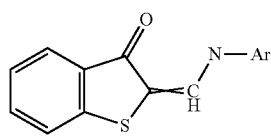

(X)

in which 2-(2-oxoethylsulfanyl)benzoic acid (XI)

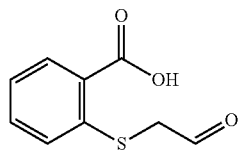

(XI)

is converted with acetic anhydride into (2-formylbenzothiophene-3-yl) acetate (XII)

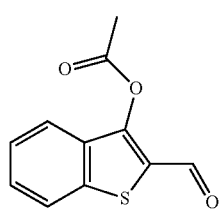

(XII)

and then reacts with lithium hydroxide into 3-oxobenzothiophene-2-carbaldehyde XIII

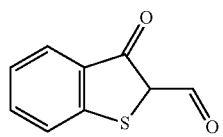 [SMILES: O=CC1Sc2ccccc2C1=O]

and results in the desired product by converting arylamines of General Formula Ar—NH$_2$.

The reaction with

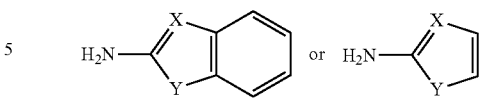

where X and Y each independently of each other can be NH, N—CH3, O, S, or with Ar—NH$^2$ where Ar is described by one of the formulae of Table 1, are preferred.

Wherever alternatives for single features such as E, Ar or Z, D etc. are laid out herein as "embodiments", it is to be understood that such alternatives may be combined freely to form discrete embodiments of the entire molecule provided as such or for use in a method or medical indication herein. Thus, any of the alternative embodiments for Ar may be combined with any of the alternative embodiments of E etc.

Structure-Activity Correlation In-vitro

Any compound for which no IC50 value could be determined in any of the assay methods shown in the Examples 1, 2 or 3, or for which IC50 values >750 μmol/l were determined, were deemed inactive. Compounds for which IC50 values <50 μmol/l were determined were assigned AA (if IC50 values of <25 μmol/l were determined reproducible with at least one method, compounds were assigned AA+). Compounds for which IC50 values <150 μmol/l were determined were assigned A; IC50 values <250 μmol/l were assigned a B, all others were assigned C.

The present invention is based on the coincidental identification of benzothiophenone compound VI

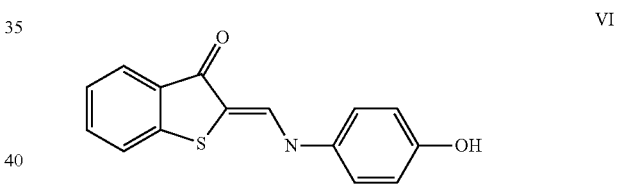

VI ((2Z)-2-[(4-hydroxyanilino)methylene]benzothiophen-3-one)

in a screen aimed at finding potential candidates for AKAP-PKA interaction inhibitors (see Klussmann et al., WO2006122546A1). Compound VI and numerous derivatives were synthesized and compared for activity in several different assay systems and in-vivo (see examples).

Despite repeated attempts, newly synthesized batches of compound VI could not be found to show significant reduction of AKAP-PKA interaction in any of the assays described herein. The reason for this discrepancy could not be clarified.

A large number of N-aryl substitutions however did show marked signals in one or more of the assays described in the Examples section. Not all substituents given in Table 1 were tested in all assay systems. From the combined data, it emerges that certain structural features predict activity in the AKAP-PKA interaction assays.

IC50 values were determined for different assays in multiple independent measurements. It appears that while values differ between methods, their ranges and ratios correlate closely between methods. All IC50 values determined were in micromolar range, while in-vivo activities were calculated to have originated from nanomolar or sub-nanomolar concentrations. The inventors presume transport phenomena or solubility issues can explain this apparent contradiction.

In the following, reference to a compounds numbered No. Y and Z in Table X is given as TX/Y,Z.

N-Aryl-Substitutions

All active compounds are substituted by an aromatic ring (or multicyclic system) on the (methylene-) amino nitrogen, wherein the aromatic ring either is a carbocyclic aryl (phenyl or naphtyl) substituted by electron-withdrawing groups such as carboxylic acid, -ester or amide groups, nitrile or nitro groups or halogens (T1/20, 25; T2/59), or wherein the aryl is a heterocycle such as a thiazole or benzothiazole.

Unsubstituted phenyl or phenyl)-substituted by electron-pushing groups such as OH or O-alkyl were not found to be active (see T3/1 to 4; the naphtyl-substituted T2/39 showed barely detectable activity). A nitro group in ortho-position gave A-type activity (ca. 100 µmol/l), whereas the same group in para resulted in much higher IC50 values. None of the N-phenyl-compounds assayed however exceeded 100 µmol/l.

Hexacyclic heteroaryl compounds showed activity, but generally of type C. Heteropentacycles generally were found to generate lower IC50 values in the A-range (<150 µmol/l). Thiazoles were explored most thoroughly, but oxazoles and imidazoles generally gave similar values where tested in surface plasmon resonance and alpha screen assays. Heteroaromatic pentacycles seem to show higher activity consistently compared to substituted phenyls, with T2/6 (unsubstituted thiazole) consistently showing an IC50 of about 50%-25% (two- to fourfold higher affinity) of that of compound T2/59 (4-benzoic acid as substituent). Absolute values for T2/1,6 were around 80 µmol/l. Adding another aromatic ring to the aromatic pentacycle generally did not abrogate activity, but generally resulted in higher IC50 values.

Substitution of the thiazole ring by an electron withdrawing group further increased affinity (decreased IC50 values) by one order of magnitude (1-5 µmol/l for compd. T2/12; cmpds. T2/13-21 at least equivalent to T2/59, monohalogen and nitrolo-substituted compds. at least half order of magnitude better than T2/59).

Surprisingly, also alkyl substituents were tolerated on the heteroaromatic pentacycles (Table 2 Cmpds. 10, 11) and indeed in these compounds, lowered the IC50 to about 50% of that of the unsubstituted mother compound. Methyl substitutions on the phenyl substituent however (T3/4) abolished activity.

Benzylic analogues of active N-aryl-substituted compounds did not show any activity in the assays performed herein.

Substitutions of Sulfur in the Benzothiophenone Ring

Oxoindanyl and (somewhat inferior: oxobenzofuranyl) analogues of compounds T2/59 and T2/23 showed generally similar activity (see T2/55-58), indicating that the sulfur atom of the benzothiophene ring is not essential for activity.

Substitution of Hexacycle in the Benzothiophenone Ring

A small number of fluoro- and ethoxy substitutions were tested in position 5 of the benzothiophenone ring. None were found to add to activity.

Exchange of Methylene Carbon by Nitrogen (Hydrazone Derivatives)

Hydrazone derivatives of exemplary active enamine compounds were synthesized (see T2/50 to 54) and found generally at least as, or more active, compared to the methylene-amine compounds.

BRIEF DESCRIPTION OF THE FIGURES

FIG. 3 shows an echocardiographic measurement of the blood flow gradient in the mouse model of Example 5a.

FIG. 4 shows the echocardiographic measurement of wall dimensions in the mouse model of Example 5a.

FIG. 5 shows echocardiographic measurement of cardiac pump function in the mouse model of Example 5a.

EXAMPLES

Example 1

Alpha Screen

Figure 1:
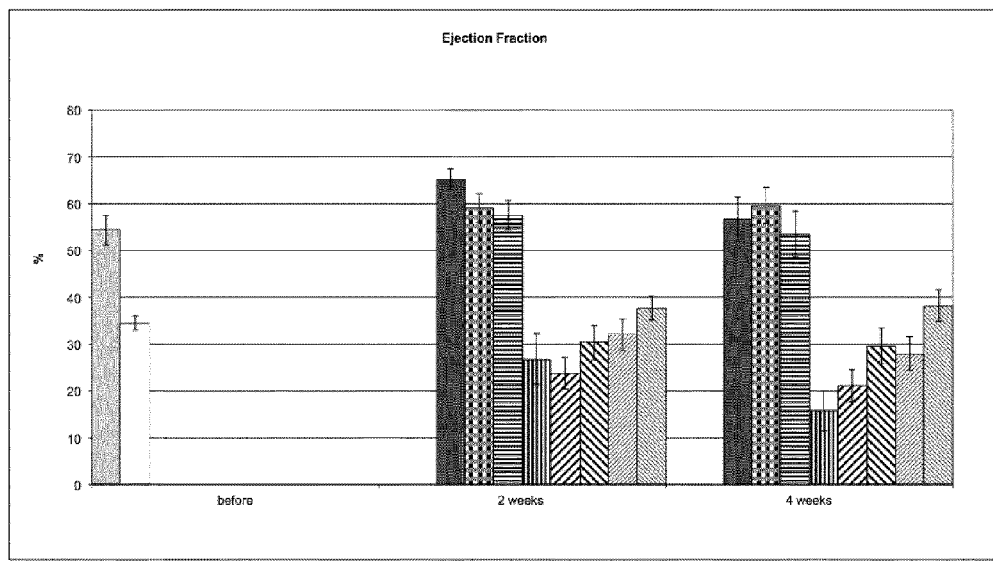
FIG. 1 shows the effect of a compound according to the invention on cardiac output over time and depending on the dose in the TAC model shown in Example 5.

The inhibition of the interaction of the alpha RII subunit of protein kinase A with AKAP18-alpha by the compounds according to the invention is determined as follows:

The general description of the alpha screen technology is known to the person skilled in the art and can be learned from the manufacturer's descriptions, which can be found among other places on the Web site of Perkin Elmer at:
http://las.perkinelmer.de/Catalog/
CategoryPage.htm?CategoryID=AlphaTech The experiment measures the suitability of candidate compounds for the inhibition of the interaction between AKAP and PKA. An AKAP-GST fusion construct is immobilized on glutathione donor beads and His-RII-alpha on Ni-chelate acceptor beads. To the extent that the partners interact, singlet oxygen from the donor beads becomes free and activates the fluorescence emission of the acceptor beads. The fluorescence emission determined in the microplate reader is proportional to the intensity of interaction of the protein partners. The IC50 is determined from the results of the measurement of several concentrations of one candidate compound.

The details of the process were as follows: Two protein Solutions A and B are produced in a buffer (phosphate NaCl buffer, 0.1% polysorbate 80, 0.1% [=1 mg/ml BSA]). These contain (A) the histidine-6-tagged fusion construct RII-alpha-His (3.125 nmol/l) and (B) the glutathione-S-transferase-tagged fusion construct GST-AKAP18-alpha-d2-10 (6.25 nmol/l). One volume unit each of protein solution and bead suspension are incorporated, specifically Solution A of the His6-tagged protein with Ni-chelate bead suspension and Solution B of the GST-fusion protein with glutathione beads (Perkin Elmer Product No. 6765302), and in doing so the concentrations are selected according to the manufacturers information. The Mixtures A and B obtained are incubated for one hour at room temperature (RT) in the dark.

Then, 5 µl of Mixture A is laid out for each hole on a 384-hole microtiter plate, and then to start with 0.5 µl of a solution of the candidate compound in DMSO is added and then 5 µl of Mixture B. The resulting reaction mixture is incubated 1 h at RT in the dark. Then, the reaction is tempered to 28.5° C., and the emitter intensity of the acceptor is determined in a microtiter plate reader after excitation of the donor at 680 nm.

The relative inhibition of the AKAP-PKA interaction is calculated following the formula:

$1-(x_c-y)/(z-y)$ where: X=average of readings (n=3) at concentration c; Y=average of measurement data from bead-bead check (n=6); Z=average of measurement data from protein-protein check (n=6).

Results:

IC50 values were determined for compounds of Table 2 in the range of $10^{-4}$ to $10^{-6}$ mol/l (see Table 2 for classification of compounds in groups AA+, AA, A, B or C).

Example 2

Surface Plasmon Resonance Analysis

Surface plasmon resonance analyses for competition in solution were performed with streptavidin-coated sensor chips (GE Healthcare, Uppsala, Sweden). The N-terminal biotinylated peptide AKAP18d-L314E was used, which is a variant of the RH-binding domains of AKAP18δ (Hundsrucker et al., *Biochem. J.* 396, 297-306, [2006]). The binding of the regulatory subunit of the human PKAII-α or RII-β onto the peptide surface of the AKAP18δ-L314E, or the inhibition of this binding to RII by the compounds of the invention, was measured on a Biacaore 3000 machine (Biacore/GE Healthcare) as previously described (Henn et al., *J Biol Chem* 279, 26654-26665 [2004]). The compounds were injected for 60 sec at a flow rate of 30 μl/min, and the dissociation phase was measured for 180 sec.

Results:

Selected compounds of Table 2 were studied. $IC_{50}$ values were measured in the range of $10^{-4}$ to $10^{-6}$ mol/l (see Table 2 for classification of compounds in groups AA+, AA, A, B or C).

Example 3

ELISA-based Assay to Measure AKAP7δ-RIIα Interaction

Multititer plates (Corning B.V. Life Sciences, Schiphol-Rijk, Netherlands) were coated with recombinantly produced PKA RIIα (15 ng/hole) by incubation with phosphate buffer containing protease inhibitors (1 h, 22° C.). The plate was then blocked with lactoprotein.

GST-AKA7δ (Hundsrucker et al., *Biochem. J.* 396, 297-306, [2006]; 15 ng/well) was incubated with and without candidate compounds on the plate for 1 h at 22° C. After washing, it was incubated with antibodies (rabbit) against AKA7δ (A18δ3) and then with a peroxidase-conjugated anti-rabbit antibody and developed with dye substrate (LumiLight Western Blotting Substrate, Roche Diagnostics, Mannheim, Germany). Luminescence activity was determined in a microplate reader (GeniosPro, Tecan, Durham, N.C., United States) at 10 msec integration.

Example 4

Immunofluorescence

The redistribution of AQP-2 channels was determined in the main cells of the collecting duct of the rat kidney (primary culture) under the influence of the compounds according to the invention, as described in Stefan et al. (*J. Am. Soc. Nephrol.* 18, 199-212 [2007]), Nedvetsky et al. (*J. Am. Soc. Nephrol.* 21, 1645-56 [2010]) and Nedvetsky et al. (*Traffic* 8, 110-123 [2007]). Example 5: "Transverse of aortic constriction" (TAC) animal model In male C57B1/6 mice (12-14 weeks old, average weight 26 g), high pressure overload induced by restricting the aorta following the method published by de Alameida et al. (*J vis exp.* 2010 Apr. 21; [38]). Control animals were treated with sham operations. The animals were observed over a period of 4 weeks after the operation, and then mini osmotic pumps were implanted intraperitoneally with a compound to be tested (0.5, 5, 50, and 100 μmol/l, corresponding to 6 μg/kg/day) (Table 2), a $β_1$-adrenergic receptor antagonist (metoprolol; 24 mg/kg/day), a $β_1$-adrenergic receptor antagonist (dobutamine; 4 μg/kg/day), a PDE3-inhibitor (milrinone; 3.0 mg/kg/d), and DMSO. Echocardiograms were done two and four weeks after implantation.

As expected, the narrowing of the aorta leads to cardiac hypertrophy and chronic heart failure in the 4-week period after surgery. The ejection fraction (ejection fraction; $E_f$) is the portion of the blood contained in the chambers of the heart that is ejected in comparison with the total volume at the end of diastole of the ventricle. FIG. 1 shows the improvement achieved by the treatment in the ejection fraction $E_f$ in comparison with untreated animals. As such, the first (left) group of bars shows the values of the ejection fraction (Y axis: ejected chamber volume in % of total chamber volume), and the second group of bars show the values after 2 weeks of treatment with Compound 59 (Table 2), and the third group of bars shows the values after 4 weeks. The following groups were measured:

Animals undergoing sham operations with
only DMSO as vehicle control (solid black bar);
Compound 59, 3 μg/kg/day in DMSO (checked bar);
Compound 59, 6 μg/kg/day in DMSO (bold crosshatched bar);
Animals undergoing TAC operations with
only DMSO as vehicle control (bold vertically hatched bar);
Compound 59, 0.03 μg/kg/day in DMSO (bold diagonal hatching to upper right);
Compound 59, 0.03 μg/kg/day in DMSO (bold diagonal hatching to lower right);
Compound 59, 3 μg/kg/day in DMSO (thin diagonal hatching to upper right);
Compound 59, 6 μg/kg/day in DMSO (thin diagonal hatching to lower right);

In healthy condition, the ejection fraction is >60%. Without treatment with the compound according to the invention, the ejection fraction in animals undergoing the operation is 20%; treatment with a compound according to the invention makes this increase to 40%, depending on the dose. It is also very important that the heart weight, shown in FIG. 2 as the ratio of heart weight to the tibia length, falls significantly in the treated animals. This means that the compound according to the invention does not show the classic positive inotropic effect that can be observed in cardiac glycosides, PDE3 inhibitors, or β-adrenergic agonists such as dobutamine.

Figure 2:
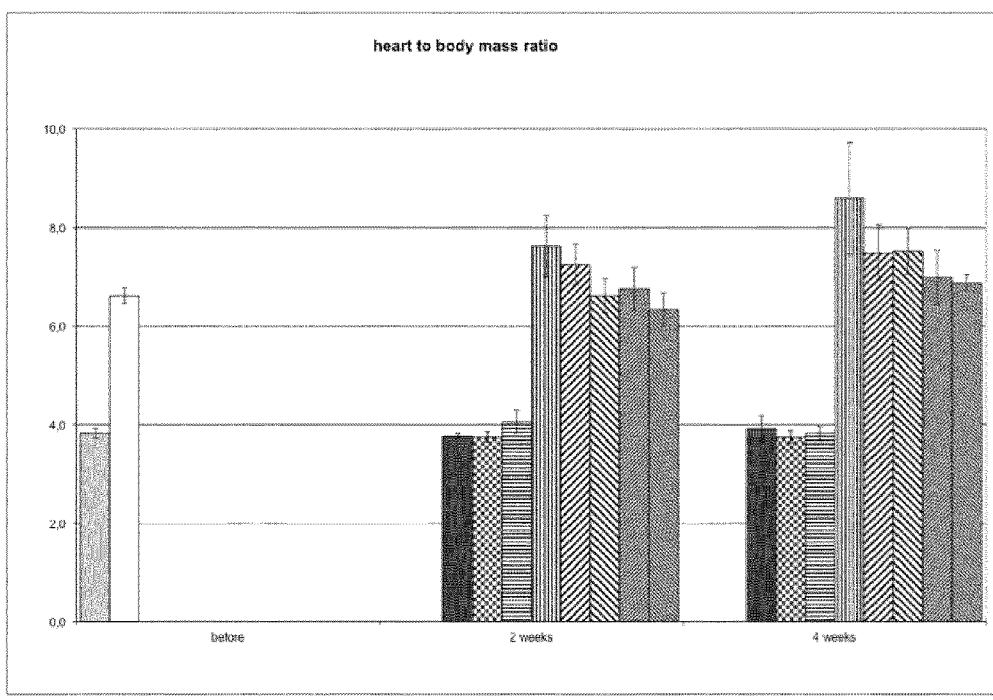
FIG. 2 shows the effect of a compound according to the invention on heart weight over time and depending on the dose in the TAC model shown in Example 5.

FIG. 2 shows the heart weight for animals undergoing sham operations (grey bar) and animals undergoing TAC operations (white bar) in the "Before" group, as well as the values at two and four weeks for the groups indicated in FIG. 1.

Furthermore, the compound according to the invention does not affect the heart rate.

Together these clearly show that the compounds according to the invention constitute prototypes of a new class of drug that reverse heart failure instead of stabilizing the patient's situation for only a limited time.

Example 5a Echocardiography in the TAC Model; In-Vivo Use of T2/15

Protocol: For intervention 12- to 14-week-old male C57BL/6 mice (Charles River Sulzfeld) were anesthetized by 2.4% isoflurane inhalation. Transverse aortic banding (TAC)

was performed by tying a 7-0 prolene suture (Ethicon) ligature around the aorta and a blunted 26-gauge needle and subsequent removal of the needle. For sham controls the suture was not tied. TAC was confirmed by echocardiography and measurement of blood flow gradient 4 weeks after surgery. Next, mini-osmotic pumps (model 1004, Alzet) with T2/15 compound/vehicle were implanted i.p. Echocardiography was performed 2 and 4 weeks with compound treatment.

For echocardiography analyses mice were anesthetized by 2.4% isoflurane inhalation and ventricular measurements were done with a VisualSonics Vevo 2100 Imaging System equipped with a 45 MHz MS-550D MicroScan transducer. The observer was unaware of the genotypes and treatments.

Differences between experimental groups were analyzed using ANOVA test followed by Bonferroni's Multiple Comparison Test using Prism Graphpad 4. Data are presented as mean±SEM. P<0.05 values were considered significant.
n-numbers:

|  | 2 weeks | 4 weeks |
| --- | --- | --- |
| Sham + DMSO | 13 | 13 |
| Sham + 0.03 µg/kg/d | 5 | 5 |
| Sham + 0.3 µg/kg/d | 5 | 5 |
| Sham + 3 µg/kg/d | 6 | 6 |
| Sham + 6 µg/kg/d | 7 | 7 |
| TAC + DMSO | 11 | 10 |
| TAC + 0.03 µg/kg/d | 5 | 5 |
| TAC + 0.3 µg/kg/d | 7 | 6 |
| TAC + 3 µg/kg/d | 7 | 4 |
| TAC + 6 µg/kg/d | 10 | 8 |

Figure 3:
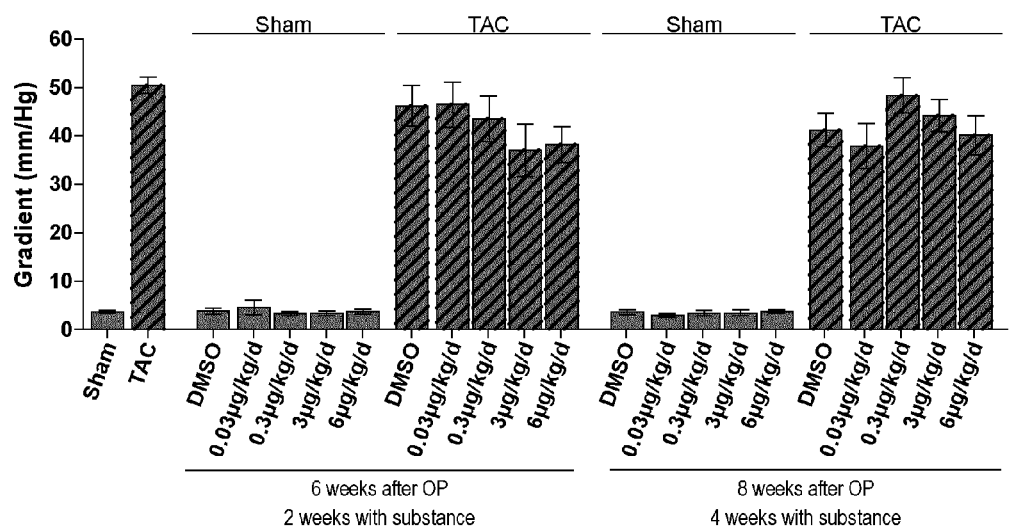
Figure 4:
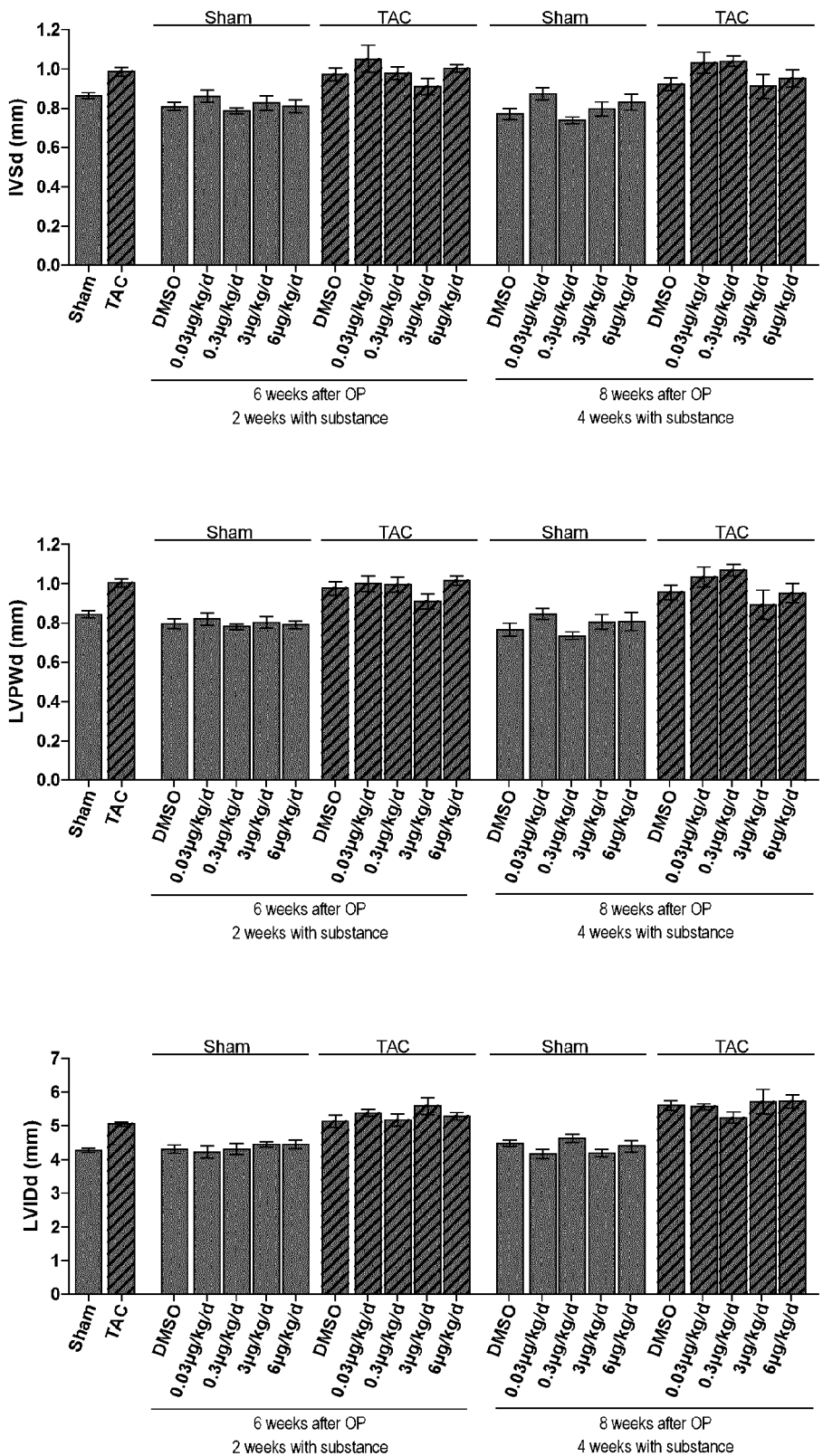

The results are shown in FIG. 3 to. FIG. 3 shows how TAC was confirmed by echocardiography and measurement of blood flow gradient 4, 6 and 8 weeks after surgery. TAC operated mice have elevated gradients (>35 mm/Hg) vs. Sham operated mice (app. 4 mm/Hg). FIG. 4 shows heart wall dimensions.

All TAC operated mice show thicker wall dimensions in comparison to sham operated mice assessed by echocardiographic measurement of IVSd (interventricular septum), LVPWd (left ventricular posterior wall), and LVEDd (end-diameter of the left ventricle) at diastole. Treatment with T2/15 had no significant effect on wall dimensions and cavity diameter.

Figure 5:
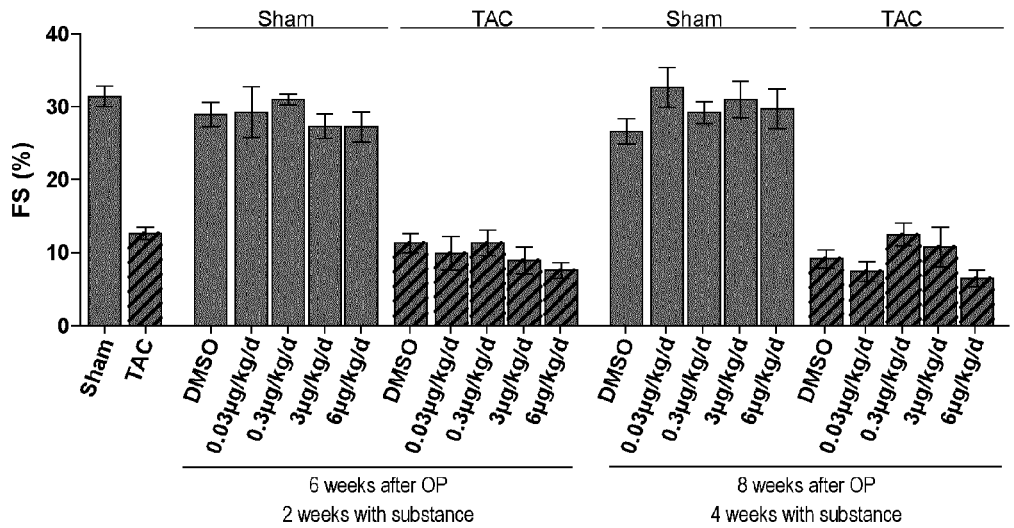
Figure 5:
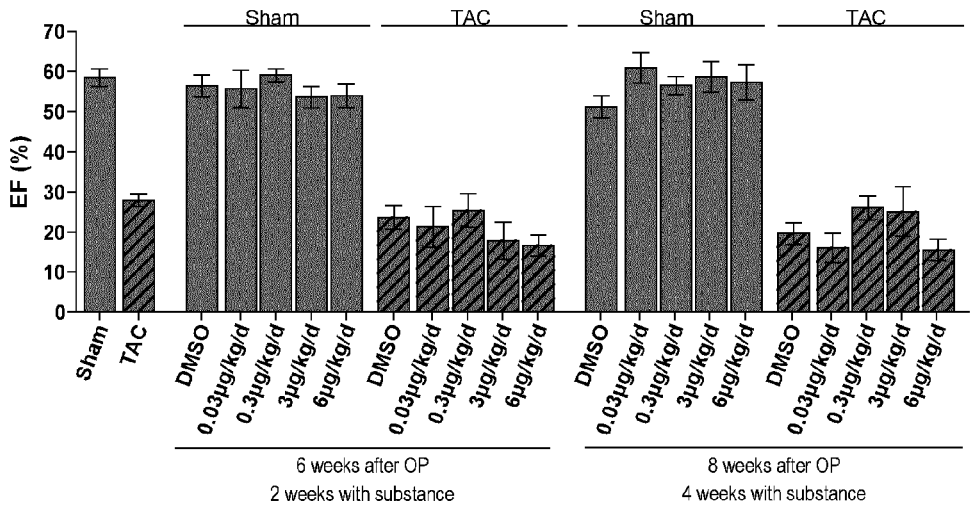
Figure 5:
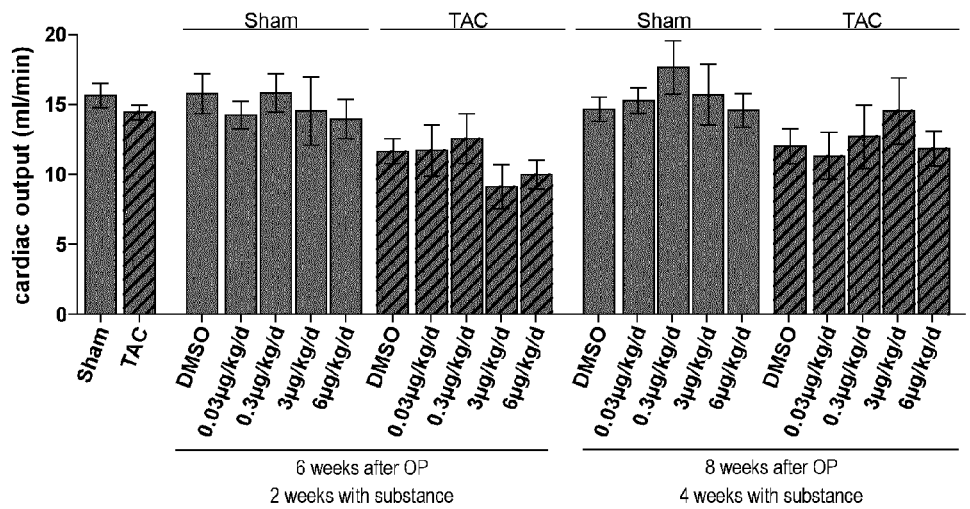
Figure 5:
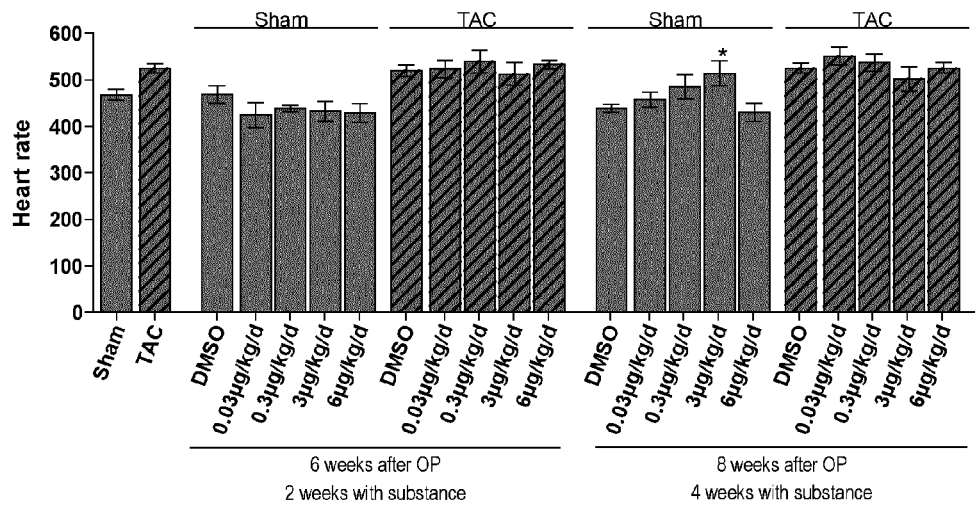

Echocardiography analysis (FIG. 5) revealed declined cardiac function of TAC vs. sham operated mice demonstrated by ejection fraction (EF), fractional shortening (FS), and cardiac output.

Figure 6:
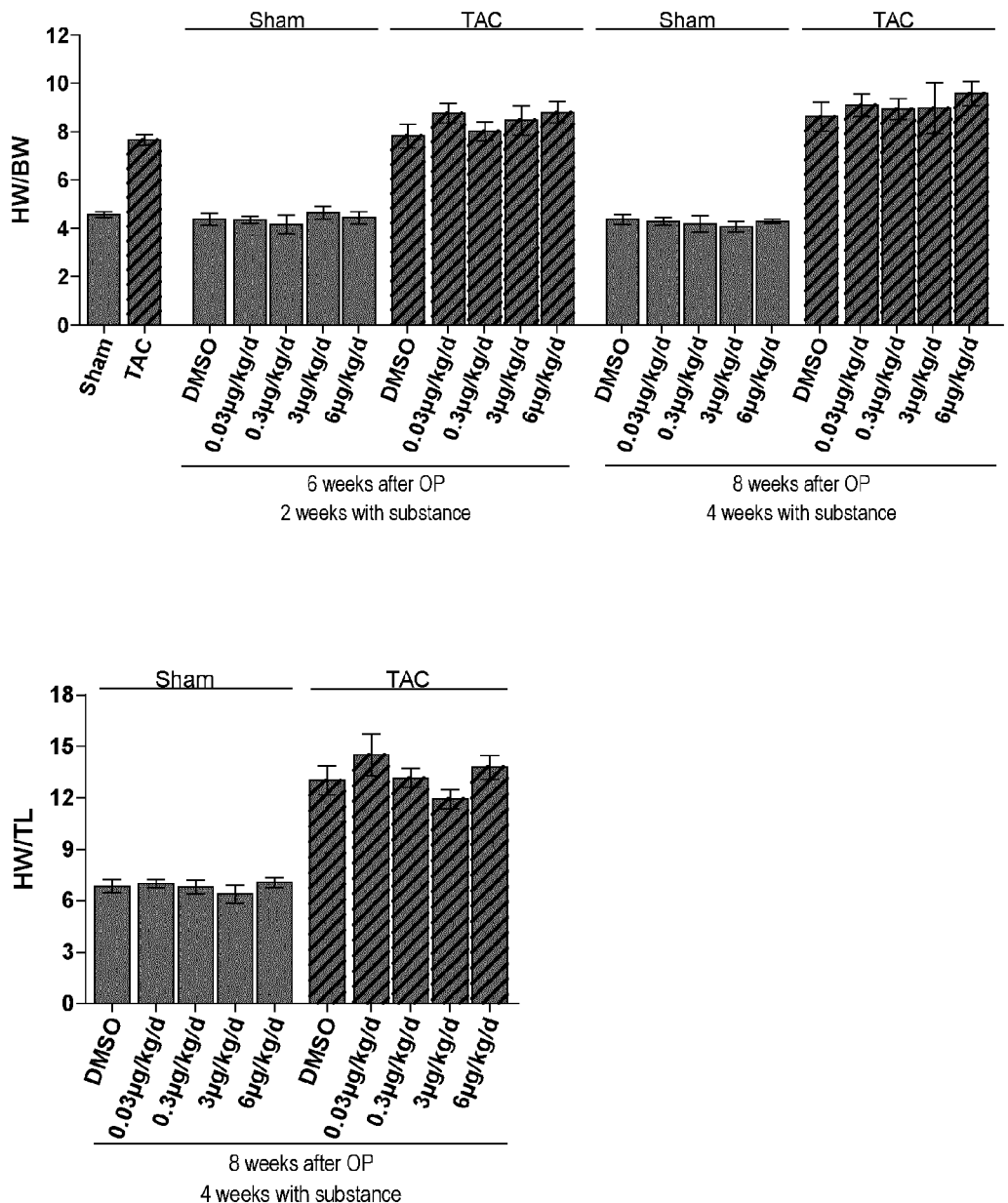
FIG. 6 shows results of the morphometric measurement of treated animals

Heart weight (HW) was normalized against body weight (BW) and tibia length (TL), respectively (FIG. 6). TAC operated mice show the expected elevated heart-to-body weight and -to-tibia length ratios in comparison to Sham operated mice. Treatment with T2/15 vs. DMSO has an effect on HW/TL.

In summary, comparison of treatment with T2/15 vs. DMSO showed that concentration ranges of between 0.3 and 3 µg/kg/d T2/15 lead to an improved function without increasing heart rate or -mass, critical parameters of therapeutically desirable outcomes.

Example 6

SIADH Model

Twelve-week-old female C57BL/6 mice were treated intraperitoneally with desmopressin (100 nmol/l) through a mini osmotic pump (Alzet, Model 1004) over 14 days. The animals received a second mini osmotic pump at the same time, with either DMSO (control) or ML-07 with a dose of 12 µg/kg/day. On Day 14, the mice were separated for 24 h into individual cages to collect metabolic data and urine. Then, the animals were killed and the organs removed for further investigations.

To study aquaporin-2 redistribution, the kidneys of the animals were analyzed with immunofluorescence microscopy after one week. In addition, paraffin sections were produced and AQP2 detected with a specific anti-AQP2 and Cy3-linked secondary antibody. They appear red on the fluorescent image. Nuclei appear blue after DAPI staining.

Example 7

Preparation of Example Compounds

Preparation of 3-oxo-2,3-dihydrobenzo[b]thiophene-2-carbaldehyde (5)

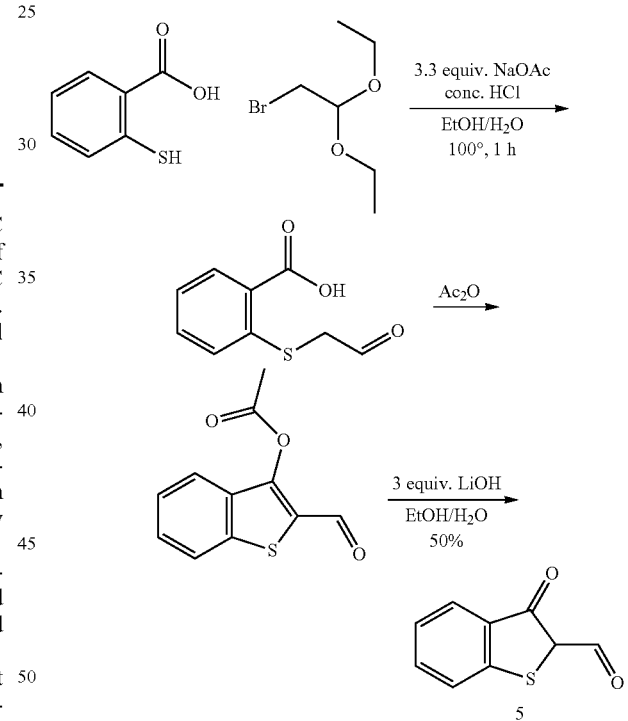

10 g (65 mmol) 2-mercaptobenzoic acid, 13 ml (84 mmol, 1.3 equiv.) bromoacetaldehydediethylacetal, and 17.6 g (215 mmol, 3.3 equiv.) sodium acetate were dissolved in 100 ml ethanol and mixed with 300 ml water. 19.5 ml (195 mmol, 3 equiv.) ccHCl were added, and the reaction mixture was heated for 1 h on a preheated oil bath at 100° C. After cooling, about 70% of the solvent distilled off in vacuum, and the remainder was left overnight at 4° C. The precipitate formed was filtered off, washed with Et$_2$O, and dried overnight on the oil pump. The Aldehyde 3 is converted in the next reaction without further purification.

The aldehyde 3 from the previous reaction was dissolved in 20 ml acetic anhydride and heated for 10 min on a preheated oil bath at 145° C. The reaction mixture was poured onto a thick layer of crushed ice and stirred until all of the ice had melted. The aqueous phase was triple-extracted with dichloromethane. The combined organic phases were dried over magnesium sulfate, concentrated in vacuum, and coevaporated with toluene.

Acetylated 3-oxobenzothiophene-2-carbaldehyde was dissolved in 20 ml ethanol and 30 ml of water, and 4.6 g (195 mmol, 3 equiv.) LiOH was added. The reaction mixture was stirred for 18 h at room temperature and acidified inclusively with 10% HCl (pH=2-3). The aqueous phase was triple-extracted with dichloromethane. The combined organic phases were dried over magnesium sulfate and the solvent distilled in vacuum. The aldehyde 5 obtained was then utilized as raw product (95% purity per LC-MS) in the next reaction.

General Procedure for Preparing 2-thioazomethylenebenzothiophenones (AAV1)

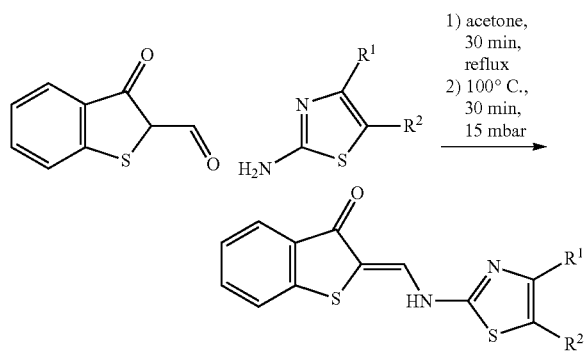

1 g 3-oxo-2,3-dihydrobenzo[b]thiophene-2-carbaldehyde (5) and 1.1 equivalents of the corresponding 2-aminothiazoles were dissolved in 30 ml acetone and heated for 10 min in a preheated oil bath at 80° C. Acetone was distilled in vacuum, and the reaction mixture was smelted for 30 min at 100° C. in vacuum (15 mbar). The solid material obtained was purified with column chromatography. Column chromatography on the silica gel (200 ml, column 4.5×60 cm, CHCl$_4$/EtOAc [4:1]) produced the desired product at a purity of ≥95% per LC-MS.

Preparation of Individual Compounds 2-((thiazole-2''-ylamino)methylene)benzo[b]thiophene-3(2H)-one Per AAV1, 317.3 mg (1.78 mmol) Aldehyde 5 and 231.8 mg (2.31 mmol) 2-aminothiazole were converted in 30 ml acetone. After column chromatography, 337 mg (73%) FMP-API-3/21 ($R_f$=0.63, CHCl$_4$/EtOAc [4:1]) was obtained as a yellow-orange solid material.

$^1$H-NMR (300 MHz, DMSO-d$_6$): δ=7.23 (s, 1 H, 4''-H), 7.34 (dd, $^3$J=2.14, $^3$J=2.06 Hz, 1 H, 5-H), 7.43 (s, 1 H, 5''-H), 7.62 (dd, $^3$J=2.14, $^3$J=2.16 Hz, 1 H, 6-H), 7.80-7.34 (m, 2 H, 4-H, 7-H), 8.53 (s, 1 H, CHNH), 11.51 (s, 1 H, CHNH).

$^{13}$C-NMR (75 MHz, DMSO-d$_6$, additional DEPT): δ=108.13 ($C_{quart}$, C-2), 113.58 (+, C-4''), 124.36 (+, C-6), 125.11 (+, C-5), 125.34 (+, C-7), 132.51 ($C_{quart}$, C-7'), 134.02 (+, 2 C, C-4, CHNH), 139.13 (+, C-4''), 143.94 ($C_{quart}$, C-3'), 162.40 ($C_{quart}$, C-2''), 186.21 ($C_{quart}$, C-3).

HPLC-ESI: $T_R$=6.3 min; m/z (%): 261 (100) [M$^+$].

2-((4''-methylthiazol-2''-ylamino)methylene)benzo[b]thiophene-3(2H)-ones: Per AAV1, 384.7 mg (2.16 mmol) Aldehyde 5 and 320.5 mg (2.81 mmol) 4-methyl-2-aminothiazole were converted in 30 ml acetone. After column chromatography, 421 mg (73%) ($R_f$=0.63, CHCl4/EtOAc [4:1]) was obtained as a yellow-orange solid material.

$^1$H-NMR (300 MHz, DMSO-d$_6$): δ=2.27 (s, 3 H, CH$_3$), 6.77 (s, 1 H, 4''-H), 7.32 (dd, $^3$J=2.20, $^3$J=2.21 Hz, 1 H, 5-H), 7.63 (dd, $^3$J=2.20, $^3$J=2.25 Hz, 1 H, 6-H), 7.74-7.80 (m, 2 H, 4-H, 7-H), 8.49 (s, 1 H, CHNH), 11.42 (s, 1 H, CHNH).

$^{13}$C-NMR (75 MHz, DMSO-d$_6$, additional DEPT): δ=17.05 (+, CH$_3$), 107.59 (+, C-5''), 124.46 (+, C-6), 125.20 (+, C-5), 125.47 (+, C-7), 132.51 ($C_{quart}$, C-7'), 134.02 (+, C-4), 134.20 (+, CHNH), 143.67 ($C_{quart}$, C-3'), 161.04 ($C_{quart}$, C-2''), 186.28 ($C_{quart}$, C-3).

HPLC-ESI: $T_R$=7.0 min; m/z (%): 275 (100) [M$^+$].

2-((5''-methylthiazole-2''-ylamino)methylene)benzo[b]thiophene-3(2H)-ones: Per AAV1, 224 mg (1.26 mmol) Aldehyde 5 and 187 mg (1.63 mmol) 5-methyl-2-aminothiazole were converted in 30 ml acetone. After column chromatography, 346 mg (84%) (RF=0.63, CHCl$_4$/EtOAc [4:1]) was obtained as a yellow-orange solid material.

$^1$H-NMR (300 MHz, DMSO-d$_6$): δ=2.34 (s, 3 H, CH$_3$), 7.11 (s, 1 H, 4''-H), 7.34 (dd, $^3$J=2.12, $^3$J=2.13 Hz, 1 H, 5-H), 7.62 (dd, $^3$J=2.12, $^3$J=2.16 Hz, 1 H, 6-H), 7.73-7.79 (m, 2 H, 4-H, 7-H), 8.46 (s, 1 H, CHNH), 11.41 (s, 1 H, CHNH).

$^{13}$C-NMR (75 MHz, DMSO-d$_6$, additional DEPT): δ=11.60 (+, CH$_3$), ~107 ($C_{quart}$, C-2), 124.34 (+, C-6), 125.06 (+, C-5), 125.28 (+, C-7), 127.83 ($C_{quart}$, C-5''), 132.20 ($C_{quart}$, C-7'), 133.99 (+, 2 C, C-4, CHNH), 136.15 (+, C-4''), 143.55 ($C_{quart}$, C-3'), ~162 ($C_{quart}$, C-2''), 186.16 ($C_{quart}$, C-3).

HPLC-ESI: $T_R$=7.0 min; m/z (%): 275 (100) [M$^+$].

2-((5''-nitrothiazol-2''-ylamino)methylene)benzo[b]thiophene-3(2H)-ones: Per AAV1, 2.23 mg (12.53 mmol) Aldehyde 5 and 1.81 mg (12.53 mmol) 5-nitro-2-aminothiazole were converted in 70 ml acetone. Acetone was distilled in vacuum and the solid material obtained was mixed with 30 ml methanol and the suspension heated to 80° C. and hot-filtered. 850 mg (23%) was obtained as a red-brown solid material.

$^1$H-NMR (300 MHz, DMSO-d$_6$): δ=7.37 (dd, $^3$J=2.16, $^3$J=2.29 Hz, 1 H, 5-H), 7.68 (dd, $^3$J=2.16, $^3$J=2.41 Hz, 1 H, 6-H), 7.77-7.81 (m, 2 H, 4-H, 7-H), 8.42 (s, 1 H, 4''-H), 8.54 (s, 1 H, CHNH).

HPLC-ESI: $T_R$=7.37 min; m/z (%): 306 (100) [M$^+$].

Example 8

Determination of pK Values by Microscale Thermophoresis (MST)

Microscale Thermophoresis (MST) were performed on a monolith NT machine (nano tember technologies, Munich, Germany) with exemplary compounds (T2/11, 15, 59) in 20 mM Phosphate, pH 7.5, 100 mM NaCl, 0.05% Tween 20 and 5% DMSO according to the general protocol provided by the manufacturer. Interaction partners were PKA subunit RIIα labelled with blue fluorescent dye NT-495; the parameters were: LED blue, LED Power 80%, Laser Power 20-80%, 25° C. A constant concentration of compounds was titrated with increasing concentrations of unlabelled PKA RIIα (50 nM, 100 nM, 250 nM, 500 nM, 1 μM, 2.5 μM, 5 μM, 10 μM, 25 μM, 50 μM, 100 μM and 200 μM).

$K_D$-values determined under these conditions:
T2/59: 88.5 μM+/−2.7 μM
T2/15: 98.1 μM+/−0.7 μM
T2/11 31.9 μM+/−1.0 μM

The invention claimed is:

1. A method for the treatment of heart failure, excessive water retention, or SIADH, the method comprising:
administering to a patient in need of such treatment a composition comprising a compound according to formula I:

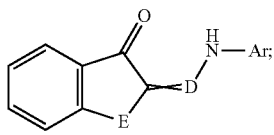

wherein:
E: means S, O, or CH₂,
D: means CH or N, and
wherein if D means CH, Ar is
  a phenyl or naphtyl moiety substituted by an electron-withdrawing group selected from halogen, a carboxylic acid or its C1-C4 alkyl ester, a carboxylic acid amide, carboxamidine, a nitrile, isonitrile, cyanate, isocyanate, thiocyanate, isothiocyanate, a nitro group or a mono-, di- or trifluoromethane group; or
  a heteroaryl residue substituted by alkyl or an electron-withdrawing group, or
  an aromatic pentacycle with at least nitrogen as a ring member;
and
wherein if D means N, Ar is a thiazole residue substituted by alkyl or an electron-withdrawing group.

2. The method of claim 1, wherein said aromatic pentacycle is substituted by hydrogen only, or by hydrogen and one electron-withdrawing group selected from the group consisting of halogen, a carboxylic acid or its C1-C4 alkyl ester, a carboxylic acid amide, carboxamidine, a nitrile, isonitrile, cyanate, isocyanate, thiocyanate, isothiocyanate, a nitro group, and a mono-, di- or trifluoromethane group.

3. The method of claim 1, wherein Ar is selected from the group consisting of cyano-, halogen,- and nitro- substituted thiazoles.

4. The method of claim 1, wherein Ar is selected from the group consisting of

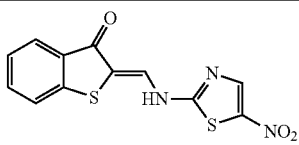

(2Z)-2-[[(5-nitrothiazole-2-yl)amino]methylene]benzothiophene-3-one;

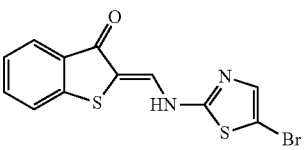 [SMILES: O=C1/C(=C/Nc2ncc(Br)s2)Sc2ccccc21]

(2Z)-2-[[(5-bromothiazole-2-yl)amino]methylene]benzothiophene-3-one; and

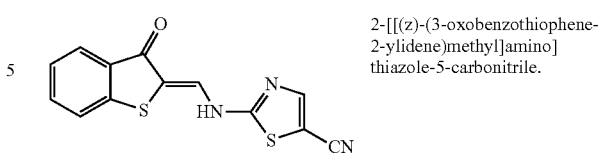

2-[[(z)-(3-oxobenzothiophene-2-ylidene)methyl]amino]thiazole-5-carbonitrile.

5. A compound of Formula V:

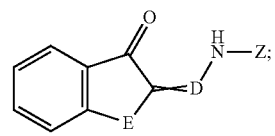

wherein
E is S (sulfur), O (oxygen), or CH₂ (methylene),
D is CH or N, and
wherein if D means CH:
Z is a pentayclic heteroaryl moiety selected from imidazole, oxazole, thiazole, thiadiazole, benzimidazole, and benzoxazole And wherein if D means N:
Z is a pentayclic heteroaryl moiety selected from imidazole, oxazole, thiadiazole, benzimidazole, and benzoxazole.

6. The compound of claim 5, wherein the pentacyclic heteroaryl moiety is substituted by one or more substituents selected from the group consisting of a halogen, a carboxylic acid or its C1-, C2-, C3- or C4 alkyl ester, a carboxylic acid amide, carboxamidine, a nitrile, isonitrile, cyanate, isocyanate, thiocyanate, isothiocyanate, a nitro group or a mono-, di- or trifluoromethane group, and a C1-, C2-, C3- or C4 alkoxide moiety.

7. A method for the treatment of heart failure, water retention, or SIADH, comprising:
administering to a patient in need of such treatment a composition comprising the compound of claim 5.

8. The method of claim 7, wherein the pentacyclic heteroaryl moiety is substituted by one or more substituents selected from the group consisting of a halogen, a carboxylic acid or its C1-, C2-, C3- or C4 alkyl ester, a carboxylic acid amide, carboxamidine, a nitrile, isonitrile, cyanate, isocyanate, thiocyanate, isothiocyanate, a nitro group or a mono-, di- or trifluoromethane group, and a C1-, C2-, C3- or C4 alkoxide moiety.

9. The compound of claim 5, wherein the compound is selected from the group consisting of:

a 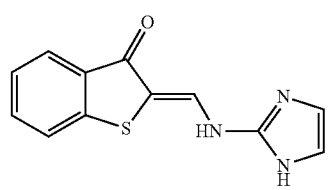 [SMILES: O=C1/C(=C/Nc2ncc[nH]2)Sc2ccccc21]

(2Z)-2-[(1H-imidazole-2-ylamino)methylene]benzothiophene-3-one;

| | | |
|---|---|---|
| b | 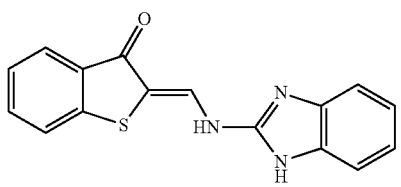 [SMILES: O=C1/C(=C/Nc2nc3ccccc3[nH]2)Sc2ccccc21] | (2Z)-2-[(1H-benzimidazole-2-ylamino)methylene]benzothiophene-3-one; |
| c | 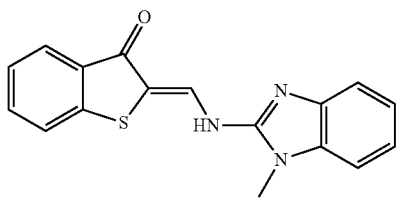 [SMILES: Cn1c(N/C=C2\Sc3ccccc3C2=O)nc2ccccc21] | (2Z)-2-[[(1-methylbenzimidazole-2-yl)amino]methylene]benzothiophene-3-one; |
| d | 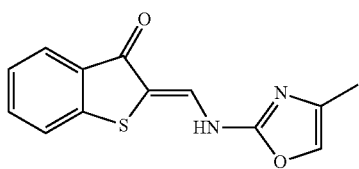 [SMILES: Cc1coc(N/C=C2\Sc3ccccc3C2=O)n1] | (2Z)-2-[[(4-methyloxazole-2-yl)amino]methylene]benzothiophene-3-one; |
| e | 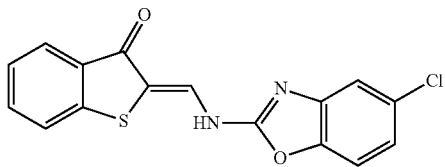 [SMILES: O=C1/C(=C/Nc2nc3cc(Cl)ccc3o2)Sc2ccccc21] | (2Z)-2-[[(5-chloro-1,3-benzoxazole-2-yl)amino]methylene]benzothiophene-3-one; |
| f | 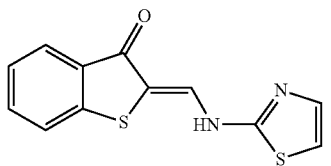 [SMILES: O=C1/C(=C/Nc2nccs2)Sc2ccccc21] | (2Z)-2-[(thiazole-2-ylamino)methylene]benzothiophene-3-one; |
| g | 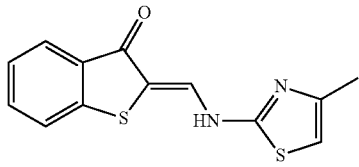 [SMILES: Cc1csc(N/C=C2\Sc3ccccc3C2=O)n1] | (2Z)-2-[[(4-methylthiazole-2-yl)amino]methylene]benzothiophene-3-one; |
| h | 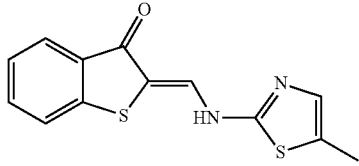 [SMILES: Cc1cnc(N/C=C2\Sc3ccccc3C2=O)s1] | (2Z)-2-[[(5-methylthiazole-2-yl)amino]methylene]benzothiophene-3-one; |
| i | 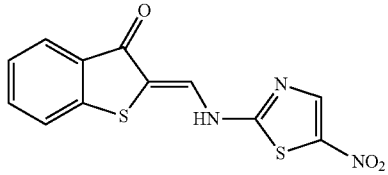 | (2Z)-2-[[(5-nitrothiazole-2-yl)amino]methylene]benzothiophene-3-one; |

| | | |
|---|---|---|
| j | | (2Z)-2-[[(5-bromothiazole-2-yl)amino]methylene]benzothiophene-3-one; |
| k | | (2Z)-2-[[(5-chlorothiazole-2-yl)amino]methylene]benzothiophene-3-one; |
| l | | 2-[[(z)-(3-oxobenzothiophene-2-ylidene)methyl]amino]thiazole-5-carbonitrile; |
| m | | 2-[[(z)-(3-oxobenzothiophene-2-ylidene)methyl]amino]thiazole-5-carboxylic acid; |
| n | | 2-[[(z)-(3-oxobenzothiophene-2-ylidene)methyl]amino]thiazole-5-carboxylic acid methylester; |
| o | | 2-[[(z)-(3-oxobenzothiophene-2-ylidene)methyl]amino]thiazole-4-carboxylic acid methylester; |
| p | | 2-[[(z)-(3-oxobenzothiophene-2-ylidene)methyl]amino]thiazole-5-carboxylic acid amide; |
| q | | n-methyl-2-[[(z)-(3-oxobenzothiophene-2-ylidene)methyl]amino]thiazole-5-carboxylic acid amide; |

-continued

| | | |
|---|---|---|
| r | 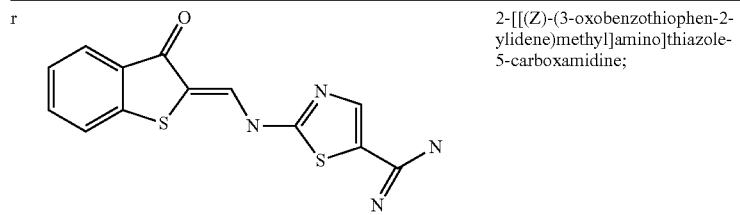 | 2-[[(Z)-(3-oxobenzothiophen-2-ylidene)methyl]amino]thiazole-5-carboxamidine; |
| s | 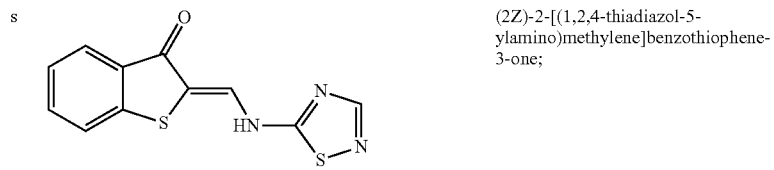 | (2Z)-2-[(1,2,4-thiadiazol-5-ylamino)methylene]benzothiophene-3-one; |
| t | 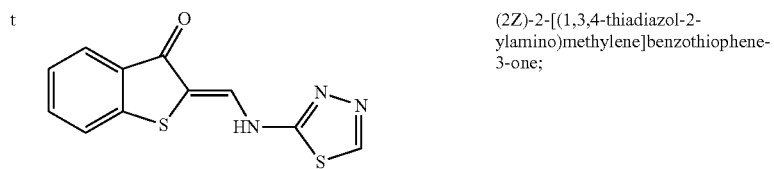 | (2Z)-2-[(1,3,4-thiadiazol-2-ylamino)methylene]benzothiophene-3-one; |
| u | 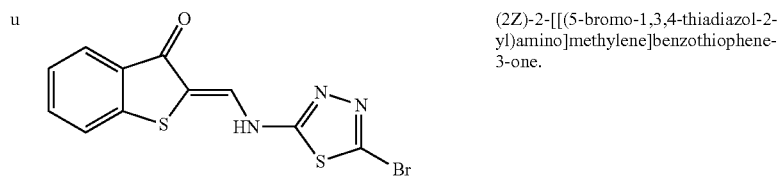 | (2Z)-2-[[(5-bromo-1,3,4-thiadiazol-2-yl)amino]methylene]benzothiophene-3-one. |

10. A method of treating a patient suffering from heart failure, excessive water retention, or SIADH, comprising administering to said patient a compound of claim 9.

11. A method of synthesizing compounds of Formula (X), where Ar designates an aryl or heteroaryl residue

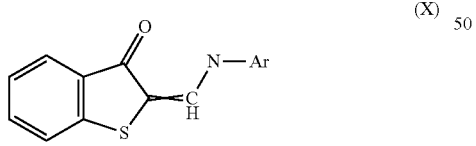 (X)

whereby 2-(2-oxoethylsulfanyl)benzoic acid (XI)

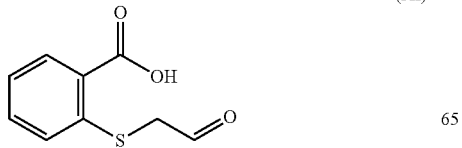 (XI)

is converted with acetic anhydride into (2-formylbenzothiophene-3-yl) acetate (XII)

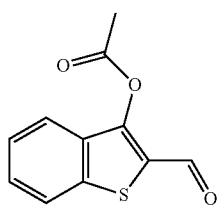 (XII)

and then reacts with lithium hydroxide to 3-oxobenzothiophene-2-carbaldehyde XIII

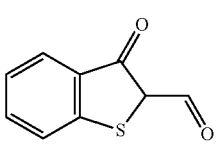 (XIII)

and results in the desired product by converting arylamines of General Formula Ar—NH$_2$, wherein
Ar is
a phenyl or naphtyl moiety substituted by an electron-withdrawing group selected from halogen, a carboxylic acid or its C1-C4 alkyl ester, a carboxylic acid amide, carboxamidine, a nitrile, isonitrile, cyanate, isocyanate, thiocyanate, isothiocyanate, a nitro group or a mono-, di- or trifluoromethane group; or
an unsubstituted heteroaryl residue, or a heteroaryl residue substituted by alkyl or an electron-withdrawing group.

12. The method according to claim 11, wherein Ar is an aromatic pentacycle with at least nitrogen as a ring member.

13. The method of claim 11, wherein said aromatic pentacycle is substituted by hydrogen only, or by hydrogen and one electron-withdrawing group selected from halogen, a carboxylic acid or its C1-C4 alkyl ester, a carboxylic acid amide, carboxamidine, a nitrile, isonitrile, cyanate, isocyanate, thiocyanate, isothiocyanate, a nitro group or a mono-, di- or trifluoromethane group.

14. The method according to claim 11, wherein Ar is selected from the group consisting of cyano-, halogen-, and nitro-substituted thiazoles.

15. The method according to claim 11, wherein Ar is selected from the group consisting of

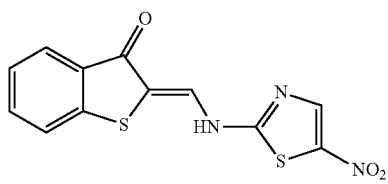 [SMILES: O=C1/C(=C/Nc2ncc([N+](=O)[O-])s2)Sc2ccccc21]

(2Z)-2-[[(5-nitrothiazole-2-yl)amino]methylene]benzothiophene-3-one;

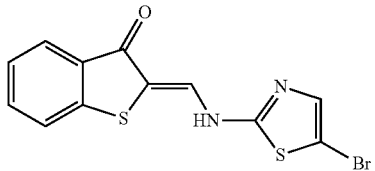 [SMILES: O=C1/C(=C/Nc2ncc(Br)s2)Sc2ccccc21]

(2Z)-2-[[(5-bromothiazole-2-yl)amino]methylene]benzothiophene-3-one; and

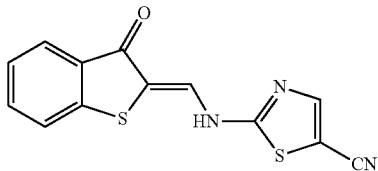 [SMILES: N#Cc1cnc(N/C=C2\Sc3ccccc3C2=O)s1]

2-[[(z)-(3-oxobenzothiophene-2-ylidene)methyl]amino] thiazole-5-carbonitrile.

16. A compound is selected from the group consisting of:

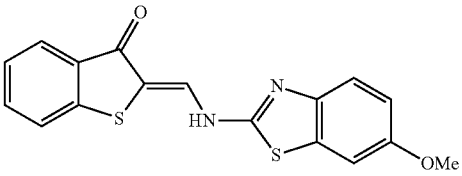 [SMILES: COc1ccc2nc(N/C=C3\Sc4ccccc4C3=O)sc2c1]

(2Z)-2-[[(6-methoxy-1,3-benzothiazole-2-yl)amino]methylene]benzothiophene-3-one;

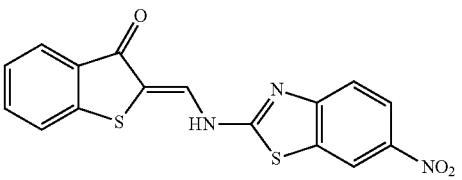

(2Z)-2-[[(6-nitro-1,3-benzothiazole-2-yl)amino]methylene]benzothiophene-3-one;

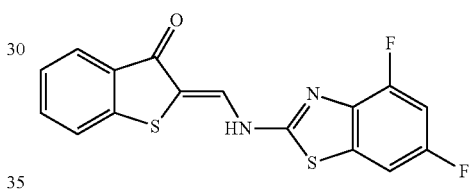

(2Z)-2-[[(4,6-difluoro-1,3-benzothiazole-2-yl)amino]methylene]benzothiophene-3-one; and

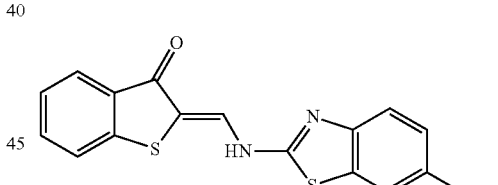

(2Z)-2-[[[(6-(trifluoromethyl)-1,3-benzothiazole-2-yl]amino]methylene]benzothiophene-3-one.

17. A method of treating a patient suffering from heart failure, excessive water retention, or SIADH, comprising administering to said patient a compound of claim 16.

* * * * *